(12) United States Patent
Basu et al.

(10) Patent No.: US 11,670,422 B2
(45) Date of Patent: Jun. 6, 2023

(54) MACHINE-LEARNING MODELS FOR PREDICTING DECOMPENSATION RISK

(71) Applicant: Microsoft Technology Licensing, LLC, Redmond, WA (US)

(72) Inventors: Sumit Basu, Redmond, WA (US); Jeremiah Wander, Redmond, WA (US); Daniel Morris, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1111 days.

(21) Appl. No.: 15/406,591

(22) Filed: Jan. 13, 2017

(65) Prior Publication Data

US 2018/0203978 A1 Jul. 19, 2018

(51) Int. Cl.
  *G16H 50/30* (2018.01)
  *G06N 20/00* (2019.01)
  (Continued)

(52) U.S. Cl.
  CPC ............ *G16H 50/30* (2018.01); *G16H 50/20* (2018.01); *G16H 50/70* (2018.01); *G06N 7/01* (2023.01); *G06N 20/00* (2019.01)

(58) Field of Classification Search
  CPC ........ G16H 50/30; G16H 50/70; G16H 50/20; G16H 50/00; G06N 20/00; G06N 7/005;
  (Continued)

(56) References Cited

U.S. PATENT DOCUMENTS

| 4,830,018 A | 5/1989 | Treatch |
| 6,251,080 B1 | 6/2001 | Kin et al. |

(Continued)

FOREIGN PATENT DOCUMENTS

| CA | 2887393 A1 | 4/2014 |
| CN | 103529684 A | 1/2014 |

(Continued)

OTHER PUBLICATIONS

Del Fiol et al., "Classification models for the prediction of clinicians' information needs," Journal of Biomedical Informatics 42 (2009) pp. 82-89. (Year: 2009).*

(Continued)

*Primary Examiner* — Brian M Smith
(74) *Attorney, Agent, or Firm* — Alleman Hall Creasman & Tuttle LLP

(57) ABSTRACT

A method for determining a risk of decompensated heart failure in a user includes receiving a first set of data that is fixed with respect to time. A machine-learning model generates one or more initial risk factors based on the first set of data. A second set of data for the user that dynamically updates over time is received from a wearable cardiovascular physiology monitor. The machine-learning model is used to generate dynamic data classifiers based on the one or more initial risk factors. Aggregate risk scores for the user are then indicated based on an evaluation of the second set of data against the dynamic data classifiers. In this way, static electronic medical records may be combined with dynamic, real-time data from wearable cardiovascular physiology monitors to provide an accurate and continuously updating risk of decompensated heart failure for a user.

10 Claims, 14 Drawing Sheets

(51) Int. Cl.
  *G06N 7/01* (2023.01)
  *G16H 50/20* (2018.01)
  *G16H 50/70* (2018.01)
(58) Field of Classification Search
  CPC .......... G06F 19/30; G06F 19/32; G06F 19/34; G06Q 50/24
  See application file for complete search history.

(56) References Cited

U.S. PATENT DOCUMENTS

| | | | |
|---|---|---|---|
| 8,475,370 | B2 | 7/2013 | McCombie et al. |
| 2004/0260185 | A1 | 12/2004 | Anderson et al. |
| 2008/0004904 | A1* | 1/2008 | Tran ....................... G06Q 10/00 705/2 |
| 2010/0016678 | A1* | 1/2010 | Beck et al. ............... A61B 5/00 600/300 |
| 2011/0224565 | A1* | 9/2011 | Ong et al. ............ A61B 5/0402 600/509 |
| 2012/0109243 | A1 | 5/2012 | Hettrick et al. |
| 2012/0179055 | A1 | 7/2012 | Tamil et al. |
| 2013/0012823 | A1 | 1/2013 | Ripoll et al. |
| 2013/0041268 | A1 | 2/2013 | Rimoldi et al. |
| 2013/0116578 | A1* | 5/2013 | An et al. ............... A61B 5/0205 600/484 |
| 2013/0226010 | A1 | 8/2013 | Hotta |
| 2014/0171749 | A1* | 6/2014 | Chin et al. ............... A61B 5/00 |
| 2014/0222804 | A1 | 8/2014 | Stivoric et al. |
| 2014/0249398 | A1 | 9/2014 | Morris et al. |
| 2014/0266787 | A1 | 9/2014 | Tran |
| 2014/0343439 | A1* | 11/2014 | Sweeney et al. .... A61B 5/0205 600/484 |
| 2015/0106020 | A1* | 4/2015 | Chung et al. ........... G06F 19/00 |
| 2015/0112208 | A1 | 4/2015 | He et al. |
| 2015/0199494 | A1* | 7/2015 | Koduri et al. .......... G06F 19/00 |
| 2015/0305632 | A1 | 10/2015 | Najarian et al. |
| 2016/0089033 | A1 | 3/2016 | Saponas et al. |
| 2016/0140834 | A1 | 5/2016 | Tran |
| 2016/0220198 | A1 | 8/2016 | Proud |
| 2018/0028114 | A1 | 2/2018 | Cronin |
| 2018/0116600 | A1 | 5/2018 | Basu et al. |

FOREIGN PATENT DOCUMENTS

| | | |
|---|---|---|
| WO | 2015069940 A1 | 5/2015 |
| WO | 2016065476 A1 | 5/2016 |
| WO | 2016097381 A1 | 6/2016 |

OTHER PUBLICATIONS

Li-wei H. Lehman et al., "A Physiological Time Series Dynamics-Based Approach to Patient Monitoring and Outcome Prediction," IEEE Journal of Biomedical and Health Informatics, vol. 19, No. 3, May 2015 (Year: 2015).*

Huddar, V. et al., "Predicting complications in critical care using heterogeneous clinical data," IEEE Access, Special Section on Big Data Analytics for Smart and Connected Health (Nov. 28, 2016) pp. 7988-8001. (Year: 2016).*

Pipke, et al., "Feasibility of personalized nonparametric analytics for predictive monitoring of heart failure patients using continuous mobile telemetry", In Proceedings of 4th Conference on Wireless Health, Nov. 1, 2013, 8 pages.

Asada, et al., "Mobile Monitoring with Wearable Photoplethysmographic Biosensors", In Journal of IEEE Engineering in Medicine and Biology Magazine, vol. 22, Issue 3, May 2003, pp. 28-40.

Dolui, et al., "ReTiHA: Real Time Health Advice and Action using Smart Devices", In Proceedings of International Conference on Control, Instrumentation, Communication and Computational Technologies, Jul. 10, 2014, pp. 979-984.

Chiarugi, et al., "Measurement of heart rate and respiratory rate using a textile based wearable device in heart failure patients", In Journal of Computers in Cardiology, vol. 35, Sep. 14, 2008, pp. 901-904.

Kim, Joseph, "Wearable device heart rate monitoring entering the consumer mainstream", http://internetofthingsagenda.techtarget.com/feature/Wearable-device-heart-rate-monitoring-entering-the-consumer-mainstream, Published on: Mar. 2014, 3 pages.

Albaghli, et al., "A vision for heart rate health through wearables", In Proceedings of ACM International Joint Conference on Pervasive and Ubiquitous Computing: Adjunct, Sep. 12, 2016, pp. 1101-1105.

Appelboom, et al., "Smart wearable body sensors for patient self-assessment and monitoring", In Archives of Public Health, vol. 72, Aug. 22, 2014, 11 pages.

Yu, et al., "Intrathoracic impedance monitoring in patients with heart failure correlation with fluid status and feasibility of early warning preceding hospitalization", In Journal of Circulation, vol. 112, Issue 1, Aug. 9, 2005, pp. 841-848.

Adamson, et al., "Hemodynamic factors associated with acute decompensated heart failure: part 2—use in automated detection", In Journal of Cardiac Failure, vol. 17, Issue 5, May 2011.

Keenan, et al., "An Administrative Claims Measure Suitable for Profiling Hospital Performance on the Basis of 30-Day All-Cause Readmission Rates Among Patients With Heart Failure", In Journal of Circulation: Cardiovascular Quality and Outcomes, vol. 1, Sep. 2008, pp. 29-37.

Fonarow, et al., "Risk Stratification for In-Hospital Mortality in Acutely Decompensated Heart Failure: Classification and Regression Tree Analysis", In Journal of the Jama Network, vol. 293, No. 5, Feb. 2, 2005, pp. 572-580.

He, et al., "Mining high-dimensional administrative claims data to predict early hospital readmissions", In Journal of American Medical Informatics Association, vol. 21, Issue 2, Mar. 2014, pp. 272-279.

Bettencourt, et al., "N-terminal-pro-brain natriuretic peptide predicts outcome after hospital discharge in heart failure patients", In Journal of Circulation, vol. 110, Issue 15, Oct. 12, 2004, pp. 2168-2174.

U.S. Appl. No. 14/750,747, "Transducing Pressure To a Non-Invasive Pulse Sensor", filed Jun. 25, 2015. 52 pages.

U.S. Appl. No. 14/750,804, "Sizable Wrist-Worn Pressure Sensing Device", filed Jun. 25, 2015. 62 pages.

U.S. Appl. No. 14/750,037, "Wearable Pulse Sensing Device Signal Quality Estimation", filed Jun. 25, 2015. 63 pages.

U.S. Appl. No. 14/750,646, "Wrist-Worn Pulse Transit Time Sensor", filed Jun. 25, 2015. 61 pages.

O'Brien, E., "Ambulatory blood pressure measurement", Irish Doctor, http://www.eoinobrien.org/wp-content/uploads/2008/06/abpm-irish-doctor-1988.pdf, Sep. 1988, 4 pages.

"ABP Monitoring—Spacelabs Healthcare", Spacelabs Healthcare website, http://www.spacelabshealthcare.com/diagnostic-cardiology/abp-monitoring, Available as early as Oct. 28, 2013, Retrieved Oct. 25, 2016, 2 pages.

"BPro—Radial Pulse Wave Acquisition Device", BPro website, http://www.bpro.ie/, Available as early as May 17, 2014, Retrieved Oct. 25, 2016, 5 pages.

"CardioSign", CardioSign website, http://www.cardiosign.com/, Available as early as Feb. 25, 2015, Retrieved Oct. 25, 2016, 1 page.

"Finapres Medical Systems", Finapres website, http://www.finapres.com/, Available as early as Nov. 30, 2002, Retrieved Oct. 25, 2016, 1 page.

"CNSystems", CN Systems website, http://www.cnsystems.at/index.php, Available as early as Apr. 4, 2012, Retrieved Oct. 25, 2016, 1 page.

"Arterial Tonometry for Blood Pressure Measurement—SR International", SRI website, https://www.sri.com/engage/products-solutions/arterial-tonometry. Available as early as Jul. 3, 2012, Retrieved Oct. 25, 2016, 2 pages.

Quick, D., "Piezo-resistive fibers enable 'blood pressure watch' with continuous monitoring", New Atlas website—Gizmag Pty Ltd, http://newatlas.com/blood-pressure-watch/27908/, Jun. 13, 2013, 4 pages.

"Non Final Office Action Issued in U.S. Appl. No. 15/443,969", dated Oct. 3, 2019, 6 Pages.

* cited by examiner

MACHINE-LEARNING MODELS FOR PREDICTING DECOMPENSATION RISK

BACKGROUND

Monitoring cardiovascular system metrics provides useful health information. Conventional cardiovascular monitoring equipment is designed to be used by trained professionals in a clinical setting.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A method for determining a heart failure patient's risk of decompensation is presented. A first set of data that is fixed with respect to time is received for a user, and one or more initial risk factors are generated by a machine-learning model based on the first set of data. A second set of data for the user that dynamically updates over time is received from a wearable cardiovascular physiology monitor. The machine-learning model is used to evaluate the second set of data based on a set of trained dynamic data classifiers. Aggregate risk scores for the user are then indicated based on the evaluation of the second set of data against the dynamic data classifiers and the initial risk factors. In this way, static electronic medical records may be combined with dynamic, real-time data from wearable monitors to provide an accurate and continuously updating risk of decompensation.

DETAILED DESCRIPTION

Figure 1:
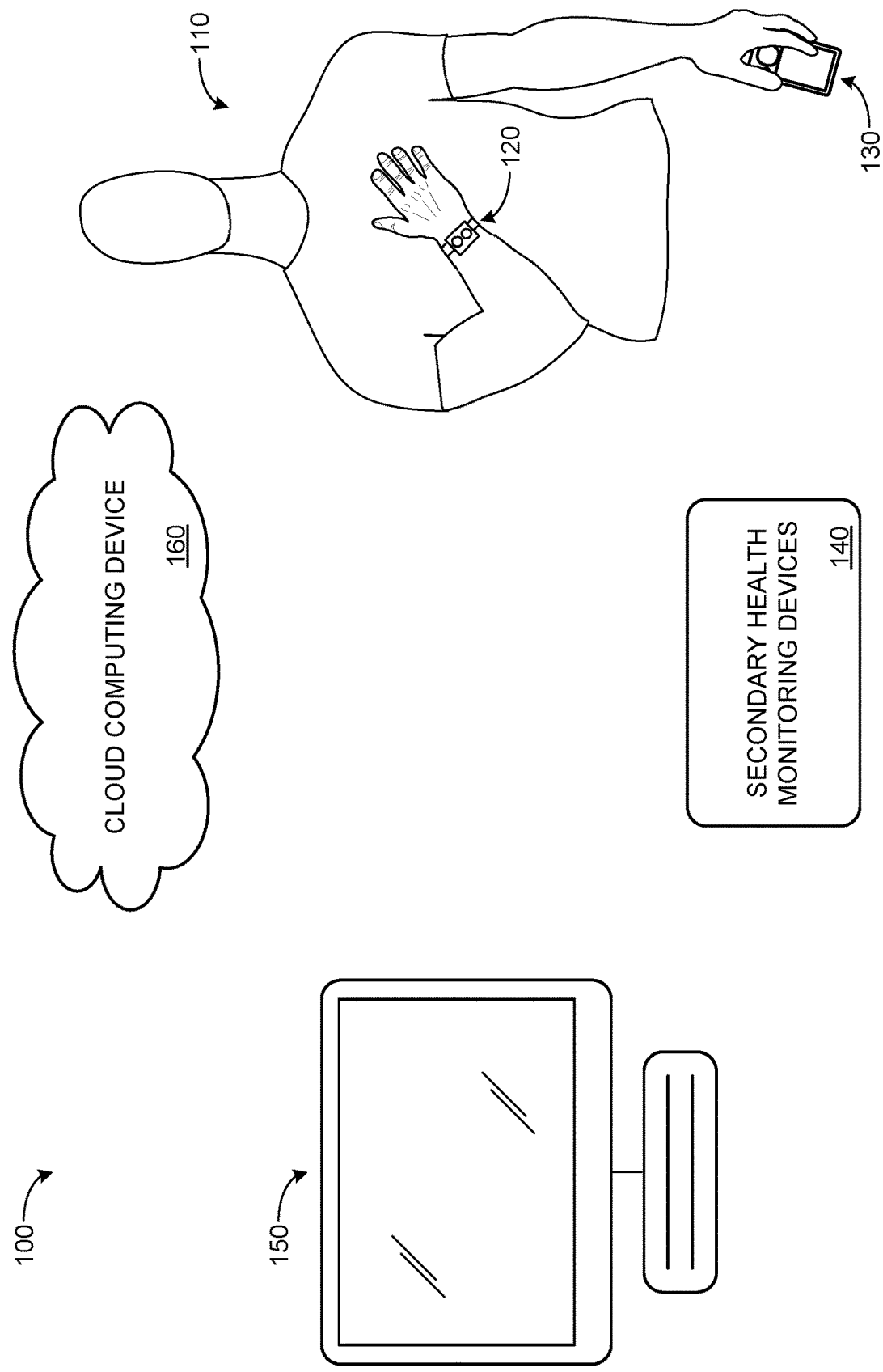
FIG. 1 shows a system for monitoring heart health of a user.

Heart failure includes a spectrum of conditions that prevent the heart from supplying enough blood to meet the body's oxygen demands. HF affects almost 6 million people in the US, and more than 20 million people worldwide. It is generally not a curable disease, but it can often be controlled. Patients whose heart failure is controlled (e.g., their bodies are compensating for their heart's inability to circulate enough blood, usually through an increase in the heart's overall effort) frequently lapse into acute episodes of decompensated heart failure (DHF), in which their bodies are no longer able to compensate for their hearts' shortcomings. DHF commonly results in hospitalization. Patients who have been recently hospitalized for heart failure (e.g., those who generally leave the hospital in a compensated state) are at particularly high risk for decompensation. Consequently, about 25% of HF patients who are discharged from a hospitalization are re-admitted to a hospital within 30 days, resulting in almost S2B of re-hospitalization costs for Medicare beneficiaries alone.

Consequently, there is an increased focus on identifying decompensation in progress before hospitalization is required. In this way, patients can be managed through phone-based interventions or outpatient clinic visits, which cost far less than hospitalization and are far less disruptive to patients' lives. Three approaches are commonly used to assess a patients' risk of decompensation and readmission to the hospital: (1) static risk estimation, (2) human telemonitoring, and (3) invasive signal thresholding.

In the first approach, hospitals use a dashboard that identifies patients at high risk at the time of discharge, who are then targeted for subsequent follow-up. This is a simple estimation approach based on a static "snapshot" of the patient's clinical data, and is unable to adapt to the myriad changes that take place after a patient is discharged.

In the second approach, hospitals employ a team of clinicians who are responsible for contacting recently discharged heart failure patients to ask them about their activity levels and symptoms (in particular weight and shortness of breath), and to make remote treatment adjustments for patients who appear to be getting worse. This process is expensive and requires significant time from caregivers. Interpreting data obtained in this manner is highly subjective, and decompensation may only be identified after it has progressed far enough to manifest as symptom changes that are apparent to the patient. In many cases, it is thought that this occurs too late for optimal or effective intervention.

The third approach depends on implanted devices, for example, either thoracic fluid monitors that are implanted in or near the heart, or pressure monitors that are implanted in the pulmonary artery. In general, these devices can be configured to generate alerts when the measured quantities exceed simple thresholds. These classes of devices are expensive, highly invasive (and thus only utilizable by certain patients), and measure only a single quantity that is compared to an empirical threshold.

Each of these approaches to risk prediction for decompensation in heart failure patients focuses on simple models based on static aspects of the patient (metrics known at the time of hospital admission, discharge, or other clinical visit) and/or on thresholding infrequently collected measurements (weight, symptom reports), or a single continuously collected measurement (pulmonary artery pressure, thoracic congestion).

This specification describes systems and methods for combining static features low-frequency non-clinical data (weight, symptom reports), and continuous dynamic data from wearable physiological sensors to provide a continuous prediction of disease state and decompensation risk in HF patients, using a machine-learning approach. A machine-learning model may be used to predict a user's risk of worsening symptoms, DHF, and/or readmission over a specific time period based on a combination of static data available at discharge and dynamic data collected by wearable sensors.

A risk score may be presented to a clinician via an electronic dashboard to allow human interpretation and intervention, but it may also be used to automatically recommend treatment decisions such as medication dose adjustments, activity restrictions, diet restrictions, etc. Risk scores may also be presented directly to the patient to reinforce behavioral recommendations and allow the patient to decide whether to seek additional care.

FIG. 1 shows an example heart-health monitoring system 100 for data generation and analysis for a user 110. User 110 may be a discharged patient who was recently hospitalized with heart failure, and has been discharged in a compensated state. User 110 is pictured wearing a wearable computing device 120, such as a wrist-worn cardiovascular physiology monitor. Wearable computing device 120 may be used to continuously collect dynamically-changing data from the user regarding the user's heart health. For example, wearable computing device 120 may collect data regarding user 110's heart rate, heart rate variability, pulse pressure wave morphology, and other features that may provide predictive value regarding the heart health of the user. Wearable computing device 120 may also provide feedback, alerts, reminders, and other indications to user 110 that may encourage self-care. An example wearable computing device is described herein with reference to FIG. 2.

Heart-health monitoring system 100 may also include a secondary computing device 130 in conjunction with wearable computing device 120. In this example, secondary computing device 130 is depicted as a smartphone, but in other examples, secondary computing device 130 may be a tablet computer, desktop computer, gaming system, Internet-connected health-monitoring server, or other suitable computing device configured to be communicatively coupled to wearable computing device 120. Secondary computing device 130 may work in conjunction with wearable computing device 120 to collect and/or process dynamic data collected by wearable computing device 120. For example, data collected by wearable computing device 120 may be downloaded to secondary computing device 130 for evaluation by a machine-learning model. In some examples, secondary computing device 130 may collect dynamic data, or facilitate the collection of data by one or more secondary health monitoring devices 140. Secondary computing device 130 may further be communicatively coupled to a clinical computing device 150 and/or a cloud computing device 160. As such, secondary computing device 130 may upload dynamic data, risk scores, and other user information for evaluation by a clinician and/or by a machine-learning model. Secondary computing device 130 may also download static data, newly available data cohorts and/or models to allow for local determination of risk scores based on dynamic data newly received at wearable computing device 120. In some examples, static data, data cohorts and/or models may be loaded directly onto wearable computing device 120.

System 100 may include one or more secondary health monitoring devices 140 that are accessible by user 110 and that are configured to provide periodic data about the health of user 110, which may then be combined with static and dynamic data in determining risk scores for user 110. For example, secondary health monitoring devices 140 may include body weight scales, ECG devices, blood pressure cuffs, exercise equipment, digital stethoscopes, and other devices that provide an indication of one or more aspects of the health of user 110. The output of secondary health monitoring devices 140 may be transferred to wearable computing device 120, secondary computing device 130, clinical computing device 150, and/or cloud computing device 160 for analysis, including use in a predictive machine-learning model.

Clinical computing device 150 may allow a clinician to monitor dynamic data and/or risk scores for user 110. Further, clinical computing device 150 may allow a clinician to input updated data, be it for user 110 or other heart failure cohorts that may in turn affect one or more machine-learning model parameters. Data may be presented to clinicians via clinical computing device 150 in the form of alerts and/or continuously varying data and risk scores. The clinician may thus incorporate this data directly into treatment decisions, including automatic and/or recommended adjustments to medication type, dosage, and/or timing. Further, outpatient visits for user 110 may be recommended and/or automatically scheduled based on the user's risk scores.

Cloud computing device 160 may facilitate data transfer between wearable computing device 120, secondary computing device 130, and clinical computing device 150. In some examples, cloud computing device 160 may provide data storage and processor power to allow for more efficient derivation of risk scores from the uploaded static, periodic, and dynamic data. Cloud computing device 160 may periodically download a current machine-learning model to secondary computing device 130, thus allowing local processing of dynamic data even in the absence of connectivity between secondary computing device 130 and cloud computing device 160. In some examples, secondary computing device 130 may upload a current machine-learning model to wearable computing device 120 to allow data acquisition, processing, and presentation to the user in one device. Data may be uploaded from wearable computing device 120 and/or secondary computing device 130 to cloud computing device 160 when network service is sufficient. Cloud computing device 160 may then periodically download data pertaining to user 110 to clinical computing device 150 for evaluation by a clinician.

Implanted devices have typically been used to generate accurate and reliable data outside of a clinical setting. Discharged patients who are provided with other types of at-home monitoring devices may be inconsistent at taking measurements, both in terms of accuracy and frequency. This data may thus not be a reliable indicator of a patient's trajectory towards decompensation. As an alternative, wearable devices may provide continuous data streams that are accurate without being invasive. A wrist-worn cardiovascular physiology monitor may provide a watch-like form factor that is familiar to a user, and that collects high-quality data via proximity to the user's radial and/or ulnar arteries.

Figure 2:
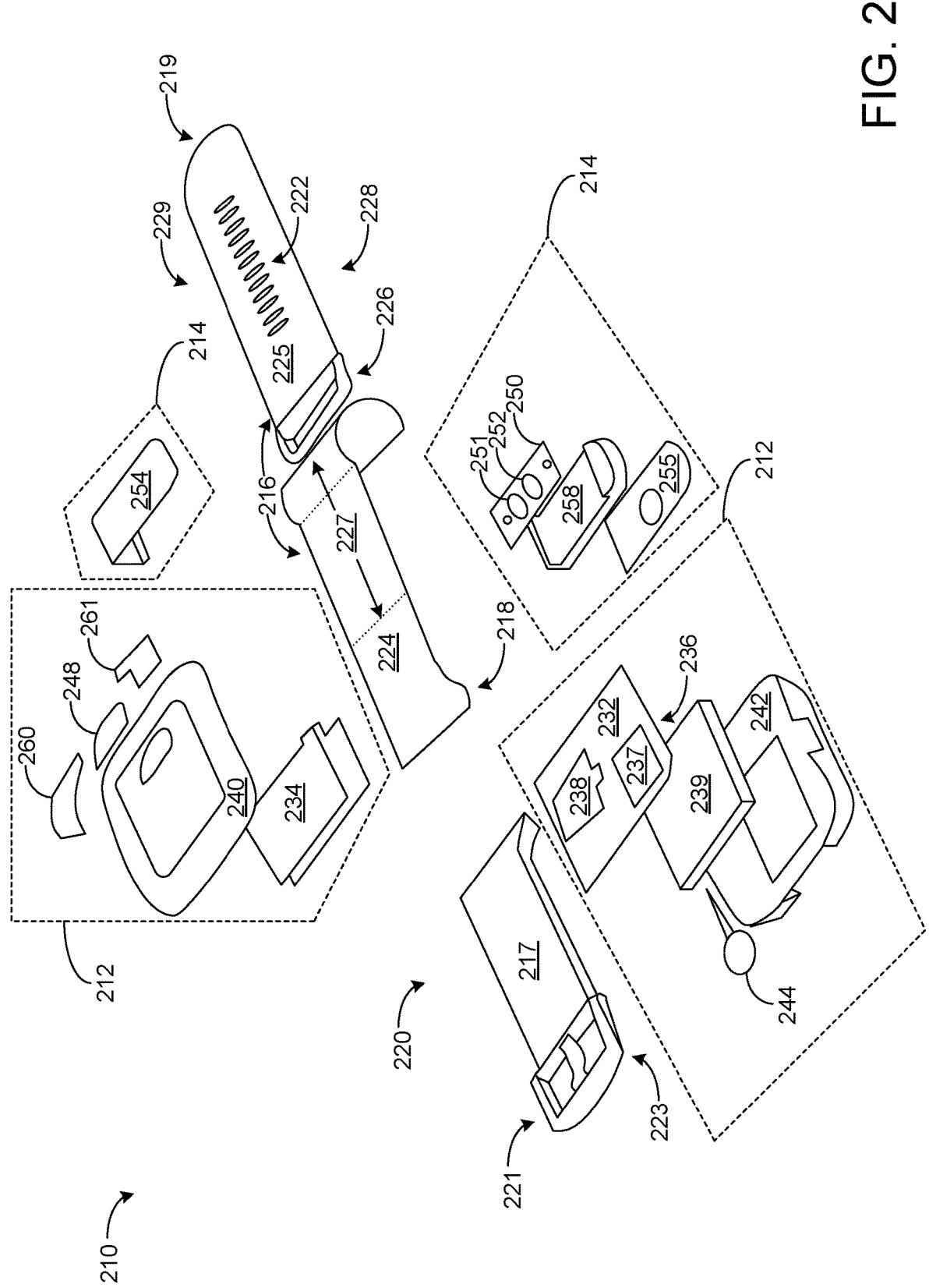
FIG. 2 shows an exploded view of a wearable electronic device.

FIG. 2 shows aspects of an example sensor-and-logic system in the form of a wearable electronic device 210. The wearable electronic device 210 may be configured to measure, analyze, and/or report one or more health parameters of a wearer of wearable electronic device 210. Wearable electronic device 210 is not limiting. One or more of the features described below with reference to wearable electronic device 210 may be implemented in another sensor-and-logic system, which optionally may have a form factor that differs from wearable electronic device 210. Wearable electronic device 210 may be an example of wearable computing device 120, and may be configured as a wrist-worn cardiovascular physiology monitor. However, dynamic health monitoring, including dynamic heart-health monitoring, may be performed using other suitable devices, both wearable and otherwise.

Wearable electronic device 210 is shown disassembled in order to depict inner componentry. The illustrated device is band-shaped and may be worn around a wrist. Wearable electronic device 210 includes a primary device 212 and a satellite device 214. Components of primary device 212 and satellite device 214 are indicated by dashed outlines. Primary device 212 may have a form function similar to the main body of a watch, and may comprise the primary user interface componentry (e.g., display, inputs, etc.) for wearable electronic device 210. Satellite device 214 may comprise pulse pressure wave transduction componentry that may enable wearable electronic device 210 to function as a wearable cardiovascular physiology monitoring device. The accuracy of pulse pressure wave transduction may be dependent on the placement of the transduction componentry relative to the wearer's skin and underlying tissue and vasculature. For example, including the pulse pressure wave transduction co entry in satellite device 214 may enable pulse pressure wave transduction at the underside of the wearer's wrist while primary device 212 is situated on the back of the wearer's wrist in a position that is familiar to watch-wearers.

Wearable electronic device 210 is shown having a first strap 216 and a second strap 217. However, in some examples a single strap may be included, and in some examples, more than two straps may be included. The straps of wearable electronic device 210 may be elastomeric in some examples, and one or more of the straps optionally may be comprised of a conductive elastomer. First strap 216 may be connected to primary device 212 at first end 218, while second end 219 is located on the opposite, distal end of first strap 216. Similarly, second strap 217 may be connected to primary device 212 at first end 220, while second end 221 is located on the opposite, distal end of second strap 217. First strap 216 comprises primary fastening componentry 222 located towards second end 219, while second strap 217 comprises secondary fastening componentry 223 located towards second end 221. The straps and fastening componentry enable wearable electronic device 210 to be closed into a loop and to be worn on a wearer's wrist.

In this example, first strap 216 comprises a proximal portion 224, which connects to primary device 212, and a distal portion 225 that comprises primary fastening componentry 222. Proximal portion 224 and distal portion 225 may be coupled together via tertiary fastening componentry 226. In this way, the distance between primary device 212 and primary fastening componentry 222 may be adjusted. However, in other examples, first strap 216 may be a single continuous strap that both connects to primary device 212 and comprises primary fastening componentry 222.

Satellite device 214 may be attached to first strap 216 at a fixed position within attachment region 227 of first strap 216, thus establishing a fixed distance between primary device 212 and satellite device 214. Primary fastening componentry 222 and second fastening componentry 223 are complementary, and thus may be adjustably engaged to adjust the circumference of wearable electronic device 210 without moving the fixed position of satellite device 214 relative to primary device 212. In this example, primary fastening componentry 222 includes discrete locations for engaging with secondary fastening componentry 223. However, in other examples, primary fastening componentry 222 and secondary fastening componentry 223 may be adjustably engaged along a continuous region.

Wearable electronic device 210 comprises a user-adjacent side 228 and an externally-facing side 229. As such, primary device 212, satellite device 214, first strap 216, and second strap 217 may each have a user adjacent, side and externally-facing side. In the closed conformation, wearable electronic device 210 thus comprises an inner surface (user-adjacent) and an outer surface (externally-facing).

Wearable electronic device 210 includes various functional components integrated into primary device 212. In particular, primary device 212 includes a compute system 232, display 234, communication suite 236, and various sensors. These components draw power from one or more energy-storage cells 239. A battery—e.g., a lithium ion battery—is one type of energy-storage cell suitable for this purpose. Examples of alternative energy-storage cells include super- and ultra-capacitors. In wearable electronic devices worn on the wearer's wrist, the energy-storage cells may be curved to fit the wrist.

In general, energy-storage cells 239 may be replaceable and/or rechargeable. In some examples, recharge power may be provided through a universal serial bus (USB) port, which may include a magnetic latch to releasably secure a complementary USB connector. In other examples, the energy-storage cells 239 may be recharged by w ireless inductive or ambient-light charging. In still other examples, the wearable electronic device 210 may include electro-mechanical componentry to recharge the energy-storage cells 239 from the wearer's adventitious or purposeful body motion. For example, batteries or capacitors may be charged via an electromechanical generator integrated into wearable electronic device 210. The generator may be turned by a mechanical armature that turns while the wearer is moving and wearing wearable electronic device 210.

Within primary device 212, compute system 232 is situated below display 234 and operatively coupled to display 234, along with communication suite 236, and various sensors. The compute system 232 includes a data-storage machine 237 to hold data and instructions, and a logic machine 238 to execute the instructions. Aspects of compute system 232 are described in further detail with reference to FIG. 8. These components may be situated within primary device 212 between top device housing frame 240 and bottom device housing frame 242. Primary device 212 may further comprise other actuators that may be utilized to communicate with the wearer, such as haptic motor 244, and/or a loudspeaker (not shown).

Display 234 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, (LCOS) array) may be frontlit via ambient light. A curved display may also be used. Further, activematrix organic light-emitting diode (AMOLED) displays or quantum dot displays may be used.

Communication suite 236 may include any appropriate wired or wireless communication componentry. In some examples, the communication suite 236 may include a USB port, which may be used for exchanging data between wearable electronic device 210 and other computer systems, as well as providing recharge power. The communication suite 236 may further include two-way Bluetooth, Wi-Fi, cellular, near-field communication and/or other radios. In some implementations, communication suite 236 may include an additional transceiver for optical (e.g., infrared) communication.

In wearable electronic device 210, a touch-screen sensor may be coupled to display 234 and configured to receive touch input from the wearer. The touch-screen sensor may be resistive, capacitive, or optically based. Pushbutton sensors may be used to detect the state of push button 248, which may include rockers. Input from the pushbutton sensor may be used to enact a home-key or on-off feature, control audio volume, turn a microphone on or off, etc.

Wearable electronic device 210 may include a plurality of additional sensors. Such sensors may include one or more microphones, visible-light sensors, ultraviolet sensors, and/or ambient temperature sensors. A microphone may provide input to compute system 232 that may be used to measure the ambient sound level, receive voice commands from the wearer, and/or receive sounds associated with heart contraction. Input from the visible-light sensor, ultraviolet sensor, and ambient temperature sensor may be used to assess aspects of the wearer's environment—i.e., the temperature, overall lighting level, and whether the wearer is indoors or outdoors. In some examples, wearable electronic device 210 may include one or more cameras, such as infrared, color, stereoscopic, and/or depth cameras.

A secondary compute system 250 is located within satellite device 214. Secondary compute system 250 may include a data-storage machine 251 to hold data and instructions, and a logic machine 252 to execute the instructions. Secondary compute system 250 may be situated between top satellite housing frame 254 and bottom satellite housing frame 255. Top satellite housing frame 254 and bottom satellite housing frame 255 may be configured to couple satellite device 214 to a fixed position within attachment region 227 on first strap 216 through the use of screws, bolts, clamps, etc. Top satellite housing r e 254 and bottom satellite housing frame 255 are shown as separate components, but in some examples, they may be coupled together by a hinge on one end, allowing satellite device 214 to be latched together around first strap 216 at the other end.

Secondary compute system 250 may be communicatively coupled to compute system 232. Satellite device 214 may mediate communication between secondary compute system 250 and compute system 232. For example, satellite device 214 may include one or more conductive contacts configured to physically intersect with one or more conductive wires extending from primary device 212 through attachment region 227 within first strap 216. In other examples, secondary compute system 250 may be coupled to compute system 232 via capacitive contact between one or more conductive contacts on satellite device 214 and one or more conductive wires within first strap 216. In other examples, a ribbon cable may extend from primary device 212 through first strap 216 such that one or more contacts on satellite device 214 can intersect with the ribbon cable when the satellite device 214 is affixed to first strap 216. In some examples, secondary compute system 250 may communicate with compute system 232 via wireless communication. In some examples, satellite device 214 may include one or more energy-storage cells. In other examples, satellite device 214 and components housed therein may draw power from energy-storage cells 239.

A pressure transducing device 258 is located within satellite device 214. When placed above the wearer's radial artery, the pressure transducing device 258 may transduce a pulse pressure wave present in the radial artery, thus functioning as a radial tonometer. The transduced pulse pressure waves may then be converted into pulse waveform signals and utilized to determine the wearer's heart rate, blood pressure, and other cardiovascular metrics and/or properties. Attachment region 227 may comprise a plurality of possible sensing locations, each possible sensing location having a different effective distance from primary device 212 along the first strap 216. In some examples, attachment region 227 may comprise a plurality of continuous possible sensing locations, while in other examples attachment region 227 may comprise a plurality of discrete possible sensing locations. By adjusting the distance between primary device 212 and satellite device 214, satellite device 214 and pressure transducing device 258 may be placed directly over the wearer's radial artery while primary device 212 is positioned on the back of the wearer's wrist. In some examples, satellite device 214 may be coupled to first strap 216 at a fixed position (e.g., at second end 219). In such examples, the distance between satellite device 214 and primary device 212 may be adjusted via interactions between satellite device 214 and first strap 216, via interactions between first strap 216 and primary device 212, and/or between regions of first strap 216.

Bottom satellite housing frame 255 is shown with an opening through which pressure transducing device 258 can establish contact with the wearer's wrist at the radial artery. Wearable electronic device 210 may be configured to instruct the wearer to adjust the position satellite device 214 relative to the radial artery if a pressure detected by the pressure transducing device 258 is below a threshold, and/or if a signal quality of the transduced pressure is below a threshold. In some examples, wearable electronic device 210 may be configured to self-adjust the position of satellite device 214 and/or the overall circumference of wearable electronic device 210.

In some examples, pressure transducing device 258 may be housed and configured to interface with a wearer's wrist independently from primary device 212. For example, pressure transducing device 258 may be worn on one wrist, while primary device 212 may be worn on the other wrist. In other examples, pressure transducing device 258 may be configured to be worn while primary device 212 is not worn. Pressure transducing device 258 may thus be configured to communicate with one or more additional computing devices, (e.g., via secondary compute system 250) such as a personal computer, tablet computer, smart phone, smart watch, gaming device, etc.

FIG. 2 shows a pair of contact sensor modules 260 and 261 situated on top device housing frame 240, which may be touchable by a wearer using fingers on the hand opposite the wrist where wearable electronic device 210 is worn. In some examples, other contact sensor modules may be included in addition to or as an alternative to contact sensor modules 260 and 261. As one example, other contact modules may be attached to user-adjacent side 228 of primary device 212, first strap 216 and/or second strap 217, and thus be held in contact with points on the wearer's wrist when wearable electronic device 210 is worn. As another example, one or more contact modules may be situated at or near secondary fastening componentry 223 on the externally-facing side 229 of wearable electronic device 210 when wearable electronic device 210 is closed into a loop, thus allowing the wearer to contact a point on their body reachable with the underside of the wearer's wrist. Additionally or alternatively, one or more contact modules may be situated on the externally-facing side 229 of the loop at first strap 216 and/or second strap 217.

Contact sensor modules 260 and 261 may include independent or cooperating sensor elements, to provide a plurality of sensory functions. For example, contact sensor modules 260 and 261 may be touchable by a wearer using fingers on the hand opposite the wrist where the device is worn, or may be placed in contact with other locations on the body of the wearer. Contact sensor modules 260 and 261 may include independent or cooperating electrodes which may provide an electrical resistance and/or capacitance sensory function, which measures the electrical resistance and/or capacitance of the wearer's skin. In some examples, one of contact sensor modules 260 and 261 may be used as a ground electrode. The ground electrode may be predetermined, or may vary based on application. Compute system 232 may use such input to assess whether or not the device is being worn, for instance. In some implementations, the sensory function may be used to determine how tightly wearable electronic device 210 is being worn. In some examples, a contact sensor module may also provide measurement of the wearer's skin temperature. In some examples, contacting multiple contact sensor modules may allow compute system 232 to determine an electrocardiogram (EKG) of the wearer.

When included, a contact sensor module located on the user-adjacent side 228 of wearable electronic device 210 may thus function as a first electrode contacting a first measurement location on a wearer's skin, while contact sensor modules 260 and/or 261 may function as a second electrode that may contact a second measurement location on a wearer's skin. When the first measurement location is located on a first effective side of the wearer's heart and the second measurement location is located on a second effective side of the wearer's heart, a controller may be configured to measure an electrical potential between the first measurement location and the second measurement location. For example, the left arm and right arm of a wearer comprise Lead 1 of an EKG. As such, when a wearer touches contact sensor modules 260 and/or 261 with skin of the non-wearing hand or arm, a voltage difference across the wearer's heart may be determined.

One or more contact sensor modules additionally or alternatively may be located on external-facing side 229 of wearable electronic device 210, such as on the externally-facing side of satellite device 214. For example, such a contact sensor module may be in the form of secondary fastening componentry 223 and/or tertiary fastening componentry 226. Due, to the kinematic restraints of the wrist, it may be easier to contact some measurement locations (e.g. EKG leads) with the device fastening componentry as opposed to contact sensor modules 260 and 261. Such a contact sensor may also be used as a third electrode that may be placed in contact with other measurement locations on the body of the wearer, for example, measurement locations on a third effective side of the wearer's heart, opposite one or more of the first and second effective sides of the wearer's heart contacted by contact sensor modules 260, 261, etc. Additional ground electrodes may be located adjacent to any additional contact sensor module. Alternatively, each contact sensor module may be divided into a conductive side and a ground side separated by an insulating layer.

Wearable electronic device 210 may also include motion sensing componentry, such as an accelerometer, gyroscope, and magnetometer. The accelerometer and gyroscope may furnish acceleration data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device 10 may also include a global positioning system (GPS) receiver for determining the wearer's geographic location and/or velocity. In some configurations, the antenna of the GPS receiver may be relatively flexible and extend into straps 216 and/or 217. In some examples, data from the motion sensing componentry may be utilized to determine a position of the wearable electronic device 210, contact sensor modules 260 and or 261, and/or pressure transducing device 258 relative to predetermined sensing locations on the body of the device wearer.

In some examples, wearable electronic device 210 may also include one or more optical sensors paired with one or more optical sources. The optical sources may be configured to illuminate the skin and/or the underlying tissue and blood vessels of the wearer, while the optical sensors may be configured to detect illumination reflected off the skin and/or the underlying tissue and blood vessels of the wearer. This optical data may be communicated to compute system 232, where the data may be used to determine the wearer's blood-oxygen level, pulse, blood glucose levels, or other biometric markers with optical signatures.

Compute system 232, via the sensory functions described herein, is configured to acquire various forms of information about the wearer of wearable electronic device 210. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

While data generated by a wearable cardiovascular physiology monitor may provide continuous monitoring of a user's heart health, the data must be analyzed and interpreted in some context in order to provide useful predictions regarding a user's heart health. In one example, static data, such as electronic medical records (EMR) for the user, may be used to determine parameters with which to analyze dynamic data generated by the wearable device. While the examples presented herein are described with regard to a wearable cardiovascular physiology monitor, such as wearable electronic device 210, other devices, such as wearable devices worn on parts of the body other than the wrist, as web as non-wearable devices, may be used to generate dynamic data regarding a user's heart health. Any such dynamic data may be used to assess a user's heart health, and such analysis may be performed on any suitable computing device.

Figure 3:
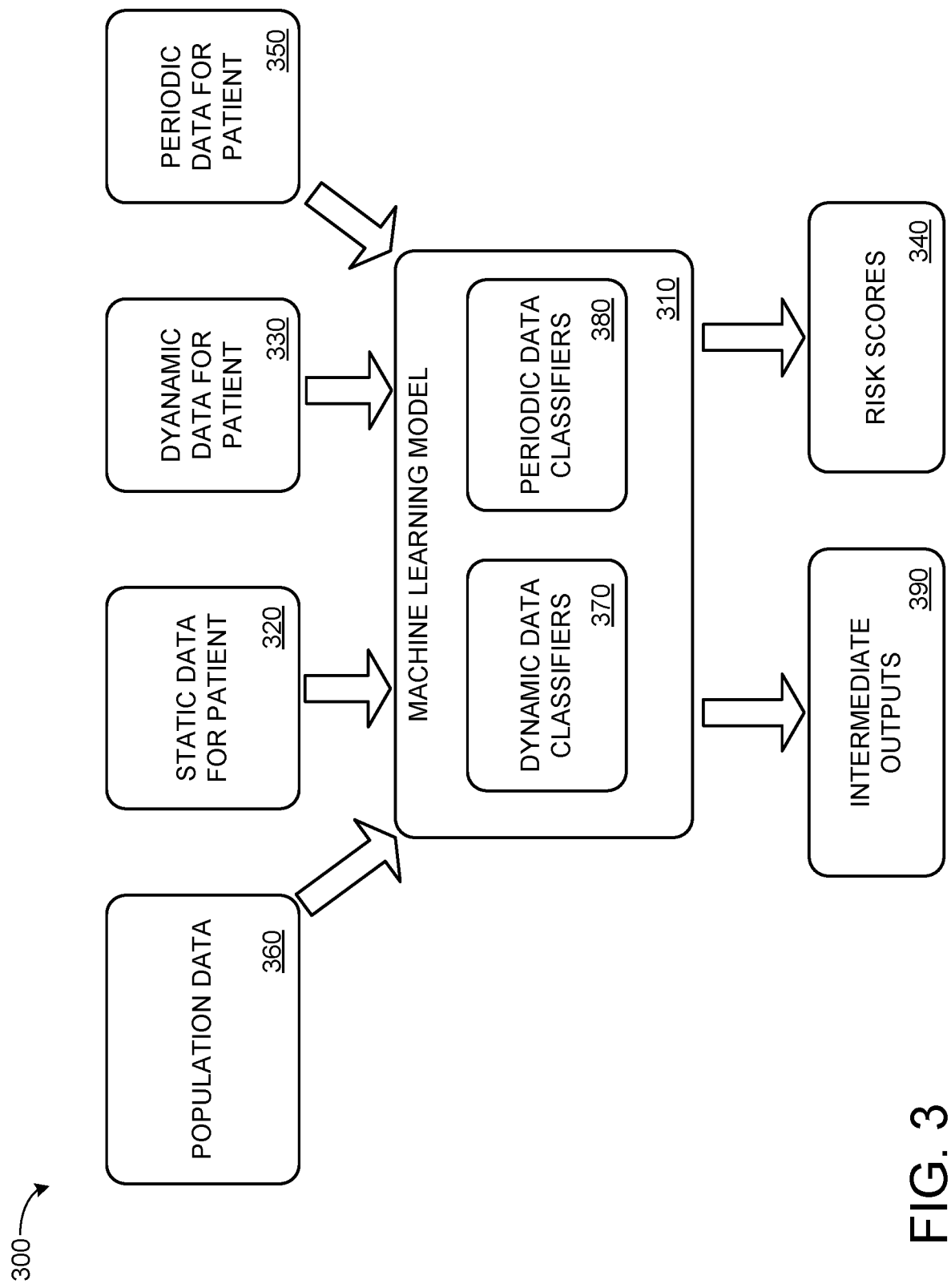
FIG. 3 shows a machine-learning system usable to determine a risk of decompensated heart failure in a user.

FIG. 3 shows an example system 300 for determining a risk of decompensated heart failure for a patient. System 300 includes a machine-learning model 310 which incorporates both static data 320 for a patient and dynamic data 330 for a patient in determining one or more risk scores 340.

Static data 320 may be derived from patient electronic medical records at the time of discharge. Static data 320 may include, but is not limited to: patient demographic information; comorbidities; medications taken before, during, and after hospitalization; vital signs; lab results; weight change during hospitalization, echocardiogram results, etc. Static data 320 may both reflect the patient's condition while hospitalized with heart failure and the patient's condition when discharged. Further, the static data may include information regarding the patient's entire health history. The static data taken during a hospitalization for heart failure may have predictive value as to the likelihood of decompensation occurring. The static data taken at the time of discharge is likely to be reflective of the patient in a compensated state. Thus, deviations from this state over time may indicate a worsening of the patient's condition.

Dynamic data 330 may be collected by a wearable computing device, either continuously or at predetermined intervals. The dynamic data may thus be indicative of heart function of the user at a given time point. For example, a wearable cardiovascular physiology monitor, such as wearable electronic device 210 depicted in FIG. 2, or any other suitable device comprising an arterial tonometer and/or an EKG sensor may collect a plurality of dynamic features that may be used as predictors of decompensation. Such features may include, but are not limited to: pulse arrival time, pulse transit time, heart rate, heart rate variability, and pressure wave morphology. The morphology of the pulse pressure wave may include numerous features that may be evaluated individually or collectively, including augmentation index, maximum systolic slope, systolic rise time, ejection time, dicrotic notch height, dicrotic notch timing, total pulse pressure, reflected wave arrival time, etc. In conjunction with signals received from an accelerometer and/or gyroscope, dynamic features such as activity level, step count, sleep time, sleep quality, posture, etc. may be used as features by the machine-learning model.

As described with regard to FIG. 1, periodic data 350 for the patient may be collected occasionally, using secondary health monitoring devices in some examples. In some examples, acquiring periodic data may require the patient to perform a task, such as standing still for 30 seconds, standing up from a sitting position, touching or adjusting a wearable or secondary health monitoring device, sitting near a bedside sensor, etc. Although periodic data 350 have lowering sampling frequency than dynamic data 330, the acquired data sets may complement each other in order to provide a more complete understanding of the patient's cardiovascular state.

Additionally, population data 360 may be used as an input to machine-learning model 310. In one example, data pertaining to a plurality of patients undergoing similar treatment and monitoring may be included in population data 360. EMR data may be collected from patients enrolled in studies where the same wearable device is being implemented for post-discharge care. Dynamic data from these patients may also be collected and included in population data 360. In some examples, population data 360 may include data from a plurality of previous heart failure patients, from a hospital's internal records, published literature, cross-hospital data sets. Such historical data may be culled from years or even decades of patient records. However, this historical data would not be paired with information generated by a wearable cardiovascular physiology monitor.

Static data 320, dynamic data 330, periodic data 350, and population data 360 may be fed into machine-learning model 310. Initially, static data 320 and population data 360 may be weighted more heavily until a threshold amount of dynamic data 330 and periodic data 350 is acquired. Static data 320 and population data 360 may be used to establish initial sets of dynamic data classifiers 370 and periodic data classifiers 380. The determined classifiers may then be used to evaluate incoming dynamic data 330 and periodic data 350, respectively.

One or more risk scores 340 may be output by machine-learning model 310, indicating a likelihood of the user developing decompensation over a set time interval. For example, risk scores 340 may be determined and output for the user indicating the user's risk of decompensation within one or more of the next 12 hours, 24 hours, 48 hours, one week, 30 days, or other suitable time interval. In some examples, the risk score(s) may be presented to a clinician. A clinician may be able to access real-time risk scores for a patient. In some examples, the clinician may receive an alert if a risk score increases above a threshold, thus indicating a user is at a heightened risk for decompensation within a set time interval. Additionally or alternatively, the clinician may receive an alert if a risk score changes by more than a threshold over a duration, thus indicating that a user may have experienced significant worsening of symptoms, and/or is not responding to treatment.

In some examples, the risk score may be evaluated by a computing device trained via machine learning to adjust treatment for a user. For example, a predetermined change in a risk score may result in an automatic or recommended adjustment in medication type, medication dose, medication timing, etc. Similarly, outpatient visits may be automatically scheduled or recommended if one or more risk scores indicate a significantly increased risk of decompensation. In some examples, the risk scores may be directly presented to the user via a wearable computing device and/or secondary computing device (e.g., as alerts or continuously varying risk scores) in order to motivate behavior changes and/or treatment compliance.

Aside from risk scores 340, one or more intermediate outputs 390 may be output by machine-learning model 310 based on the static data and dynamic data. For example, machine-learning model 310 may output reminders of behavioral instructions (e.g. dietary restrictions) when it appears that a user's risk is increasing. Shortness of breath (dyspnea) is a key indicator of decompensation. Elements of dyspnea are detectable by a wearable cardiovascular physiology monitor. Specifically, breathing rate and breathing depth manifest as changes in pulse-wave morphological features, and may also impact heart rate variability. As such, an intermediate output 390 may include predicted breathing patterns for the user based on the collected dynamic data. Detectors for such breathing patterns may then be used as dynamic data classifiers 370 and the outputs of those detectors may be used as a dynamic feature by machine-learning model 310.

Combining the different types of data input to machine-learning model 310 presents numerous challenges. Firstly, static data 320 and dynamic data 330 may represent different sets of physiological features, and are thus not directly combinable. Static data 320 and dynamic data 330 also occupy different time courses—one data set is aging and not changing, the other data set is constantly updating.

Further, it may be preferable to have the machine-learning model learn aspects of both static data 320 and dynamic data 330 separately, but join the two data sets together in generating risk scores 340 and intermediate outputs 390. A more robust model may be generated when each data set informs the other data set(s).

Data available for training machine-learning model may be broken into several categories. For the current patient, there exists EMR (static) data and dynamic data derived from a wearable cardiovascular physiology monitor. The EMR data may include thousands of features for one medical record, while the dynamic data may include tens of features for one medical record. EMR data and dynamic data may also exist for all other patients (current cohort) utilizing the same (or similar) wearable cardiovascular physiology monitors. The current cohort EMR data may include thousands of features for hundreds of medical records, while the current cohort dynamic data may include tens of features for hundreds of medical records. Additionally, EMR data may be accessible from an historical cohort, comprising thousands of features from millions of patient records.

For the development and training of machine-learning models to be used along with a wearable cardiovascular physiology monitor, a default method is to use data where all features are available for all records, which would restrict inputs to the model to those derived from patient data within the current cohort. Unfortunately, EMR data is inherently very high-dimensional, in that it contains all possible facts about a patient's history, any of which could be considered a feature. As such, training models on historic data with millions of records would be sensible, but may not be so with only hundreds of records available as in a current cohort. One challenge for model development, then, is to make use of the EMR information in the current cohort to train machine-learning models without being affected by data dimensionality. Data available from heart failure patients that are not involved in the current cohort may provide a significantly larger data set, though dynamic data may not be available from these patients. Another challenge for model development is thus to integrate the broad EMR data into machine-learning models despite the lack of dynamic data for those patients.

FIGS. 4A-4G illustrate numerous methods for training and implementing machine-learning models for predicting decompensation in heart failure patients. Herein, $x^i$ refers to dynamic (real-time) data from a wearable cardiovascular physiology monitor for a particular patient i; $x_j^i$ refers to feature j (e.g., ventricular contractility) from patient i. Similarly, $r_j^i$ refers to feature j from the EWER data for patient i. The device and EMR data from the entirety of a current cohort are represented as X and R respectively, while historic EMR data is represented as $R^H$. Risk predictions from these models are notated as y. Note that because the features from the device $x^i$ are continuous, i.e., they could be written as $x^i(t)$, and a continuous time risk score $y^i(t)$ can be produced from these models. Note also that data sizes are meant to be illustrative of relative sizes; actual data sizes and feature dimensionalities may vary.

One approach would be to combine all of the data into a single classifier or regressor for risk. To do this, only X and R from a current cohort could be used without the benefit of any historical data. This would result in hundreds of records having many thousands of features being input into the machine-learning model. While it would be possible to train a model this way with aggressive feature selection and regularization, such a model may also be overfit and unlikely to be useful in practice. A training model for this approach is shown at 400 of FIG. 4A. As shown, the model is underspecified, having far fewer records than features. As such, the model may be overfit. At 405, a production model for this approach is shown. As shown, all static data and dynamic data are concatenated together and fed into the machine-learning model to produce a risk score (y).

Another approach that allows the use of at least some part of all of the available data includes using only those features $x_j$ in X that are also available in R—for instance, features like heart rate or body temperature are available in both the static data and the device-generated dynamic data. Such a model may then be trained using all EMR data, both R as well as $R^H$, including (but not limited to) those dynamic features $r_x$ that are also produced by the device. In deployment, the model would then use features from $r^i$, imputing values from $x^i$ for $r_x$. A benefit of this approach is the ability to use all available EMR data. However, a limited part of the dynamic data generated by the device may be used.

Figure 4A:
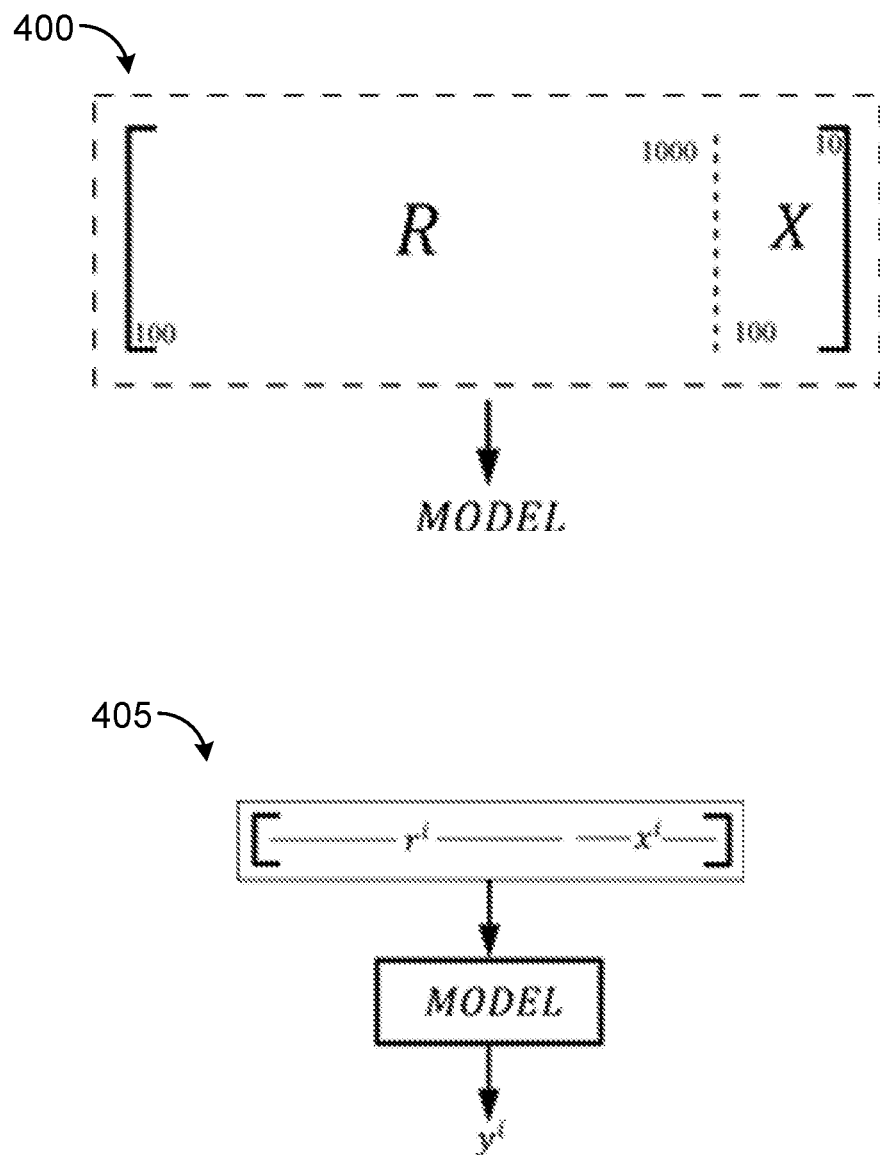
FIG. 4A shows an example machine-learning model for predicting a risk of decompensated heart failure in a user using a single classifier approach.
Figure 4B:
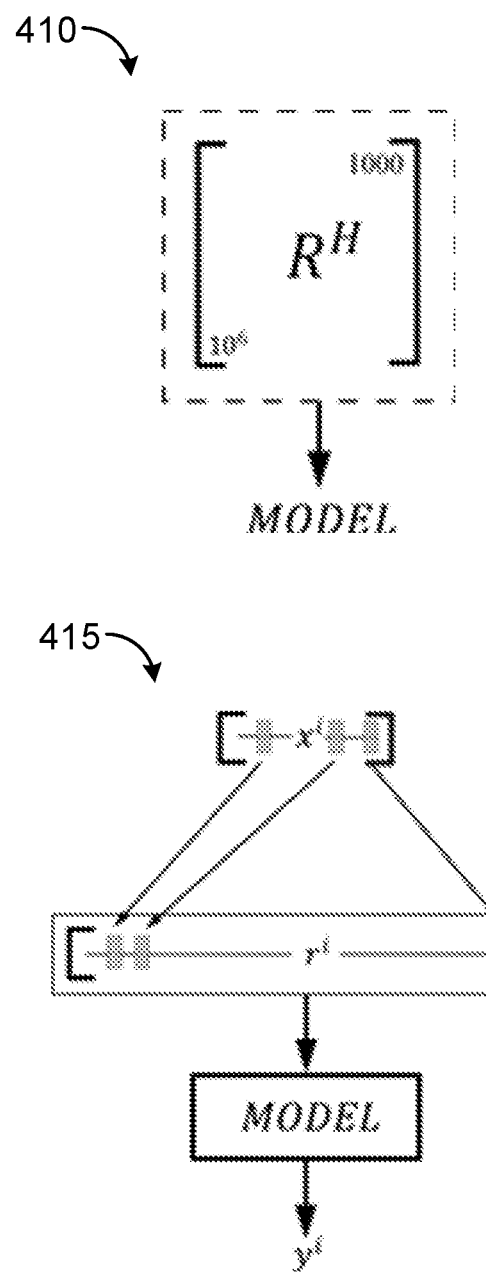
FIG. 4B shows example machine-learning model for predicting a risk of decompensated heart failure in a user using common static and dynamic features.

A training model for this approach is shown at 410 of FIG. 4B. As shown, all data from both the current cohort and historical cohort of EMR data may be used with all available features, including those features that are also available from the device. At 415, a production model for this approach is shown. The entire EMR record of the patient, $r^i$, is used as input, with those dynamic features $r_x$ available from the device imputed into the machine-learning model.

An additional approach that may allow using all available features would be to combine the models via the risk scores (of each separate model) instead of combining the data at the feature level. $R^H$ may then be used to train the development models of risk based on the EMR data alone or to further inform existing models. In parallel, a model can be trained on X to predict decompensation risk from the device-derived dynamic data. The outputs of these models, as applied to $x^i$ and $r^i$ may then be combined with a combination factor α which can be adjusted with the size of $x_i$. In other words, as more dynamic data is generated from patient i, the model may rely less on static data from their EMR. A training model for this approach is shown at 420 of FIG. 4C. As shown, there are two models, one for the static EMR data and one for the device-derived dynamic data. The former can be trained on historical EMR data. At 425, a production model for this approach is shown. Static and dynamic data are fed into separately trained machine-learning models. The predictions of the two models are then combined to generate a risk score.

Figure 4C:
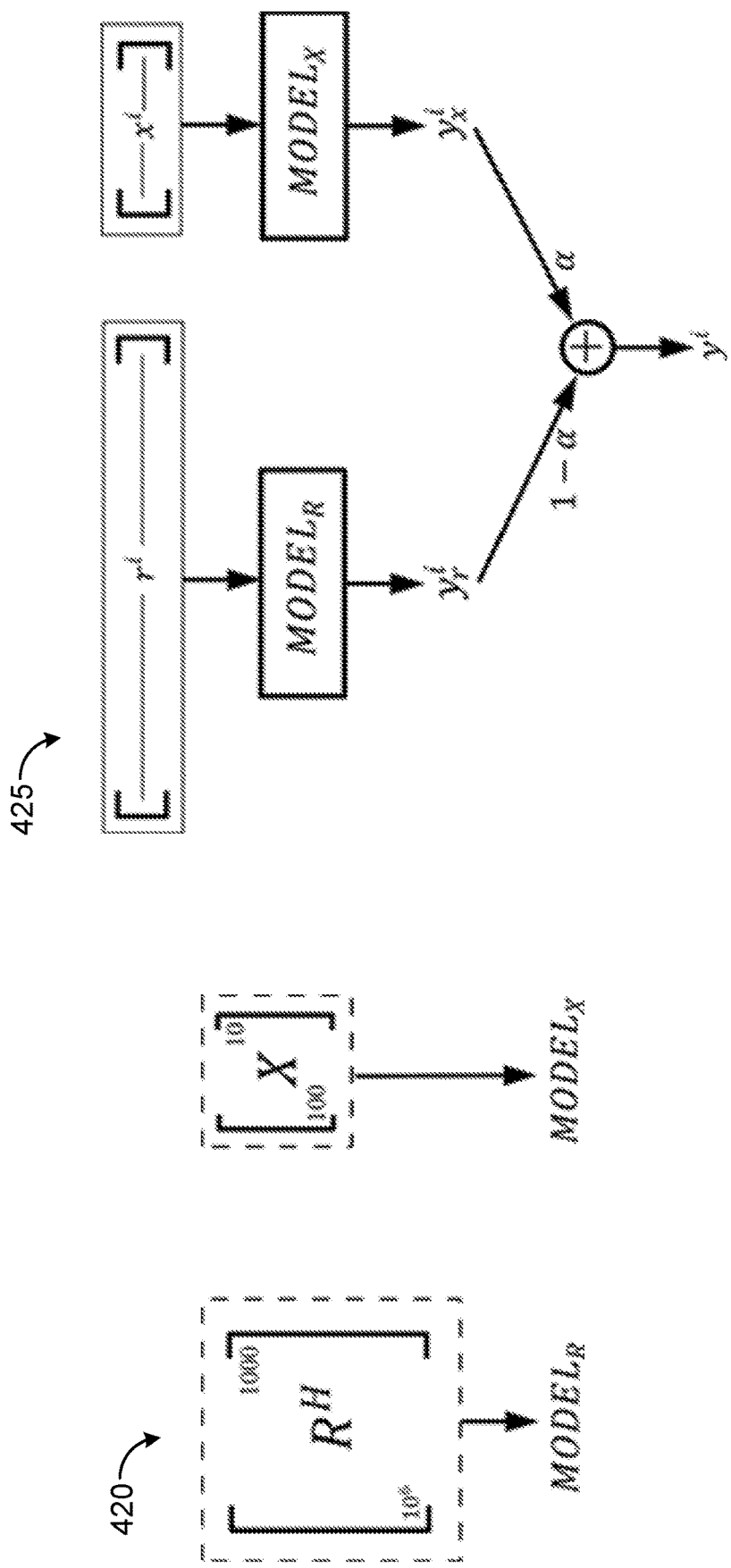
FIG. 4C shows an example machine-learning model for predicting a risk of decompensated heart failure in a user using a combination of risk scores.

Two benefits of the approach shown in FIG. 4C are that the two models can be trained separately on appropriate amounts of data and thus can perform reasonably and that historical data/models can be combined with dynamic data generated by a wearable device. However, a downside is that only one output is used from each model (static or dynamic), and thus the approach may potentially miss out on the richness of available information in terms of fusing the outputs To address these problems, the risk output of an EMR-based model may be used as an additional feature in a model based on dynamic features in X. In other words, if there are 10 features derived from the wearable device, the risk from the EMR-based model will be incorporated as an $11^{th}$ feature. The benefit of this approach over those previously described is that the model is trained to effectively use this risk score in combination with other features.

Figure 4D:
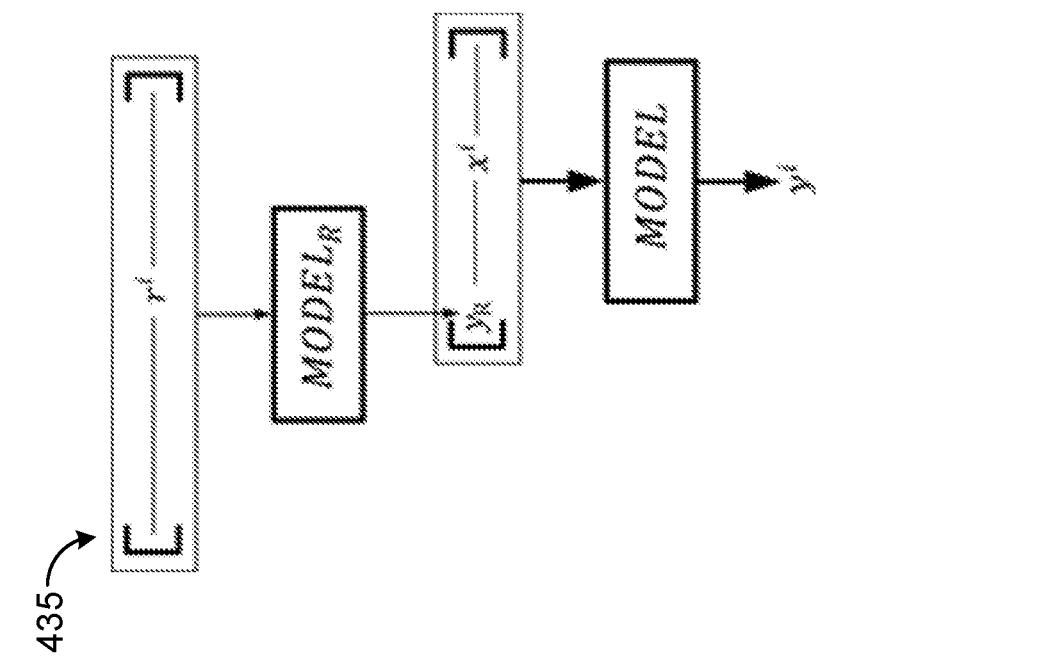
FIG. 4D shows an example machine-learning model for predicting a risk of decompensated heart failure in a user using risk as a model feature.
Figure 4D:
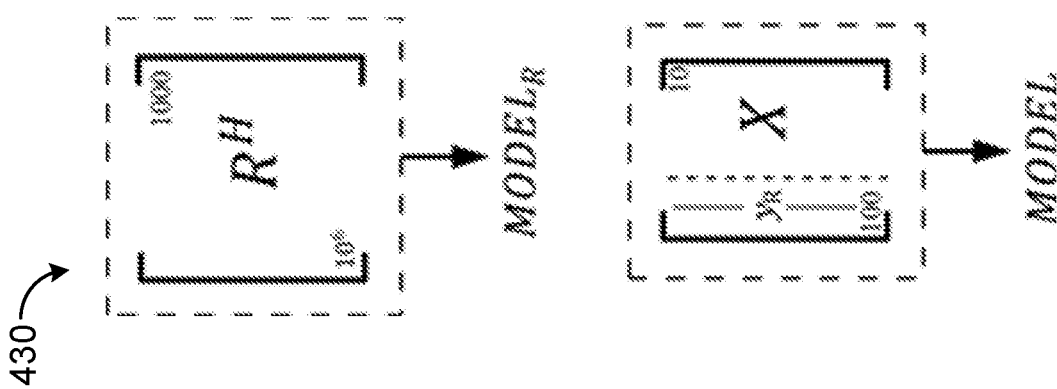

A training model for such an approach is shown at 430 of FIG. 4D. There are two models that are trained in series. The first is for static data, and the model can be trained on historical cohort data. Once trained, the model can be applied to current cohort data to produce risk values for all subjects. Those values are then concatenated with the dynamic data derived from the wearable device to form the training data for the final model. A production model for this approach is shown at 435 of FIG. 4D. The static data is fed through the first model to produce a risk score, which is concatenated with the dynamic features to form the feature vector for the final model.

The downside of this approach, as with the approach described with regard to FIG. 4C, is that the richness of the EMR data is still being compressed into a single value, which has limited potential for capturing the interactions between the static and dynamic data In order to capture more of the richness from the EMR data, another approach involves using human expertise to identify key conditions which are deemed to be relevant to decompensation prediction, and then using these as features. Some of these conditions may be simple binary variables, such as the use or non-use of a certain medication. Others may be more complex and require their own predictors/models, either because they are modeling future conditions (e.g., risk of future stroke or heart attack) or simply due to the noisy nature of EMR data. For example, they may not appear as variables in the records but can be inferred by analysis of the text (e.g., smoking history, family history of CV conditions). To continue the previous example, these features can there be introduced as the $11^{th}$ through $11+N^{th}$ features in addition to the data in X.

The main benefit of such an approach is that the EMR data may be used in a richer way. The number of features added may need to be limited given the limited size of X; otherwise an underconstrained data situation akin to that described with regard to FIG. 4A may result. The primary downside of this approach is that the features chosen by clinicians/data analysts may not be optimal for predicting HF.

A variant of this approach would be to select features from existing models for decompensation risk from EMR data that have the highest weight. However, a high weight does not necessarily mean that when taken alone, those features will be effective in the absence of the others. This may also limit the selection to those individual features used in the EMR model, whereas unknown combinations (such as those underlying the predictors for conditions identified by the clinicians) may provide the greatest predictive power.

Figure 4E:
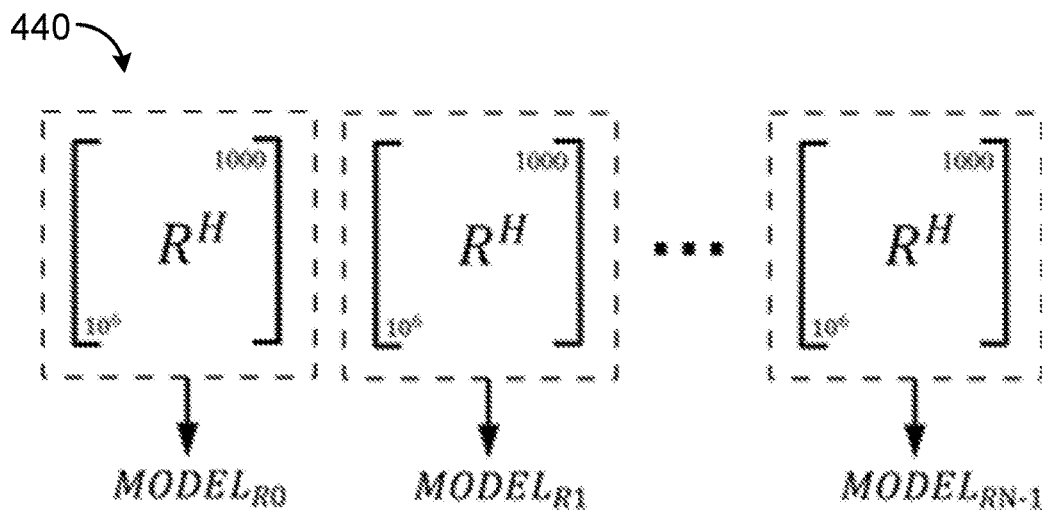
FIG. 4E shows an example machine-learning model for predicting a risk of decompensated heart failure in a user using electronic medical record derived conditions as features.
Figure 4E:
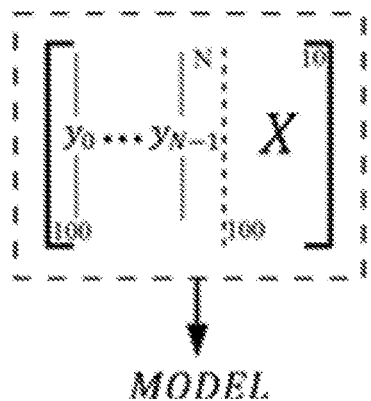
Figure 4E:
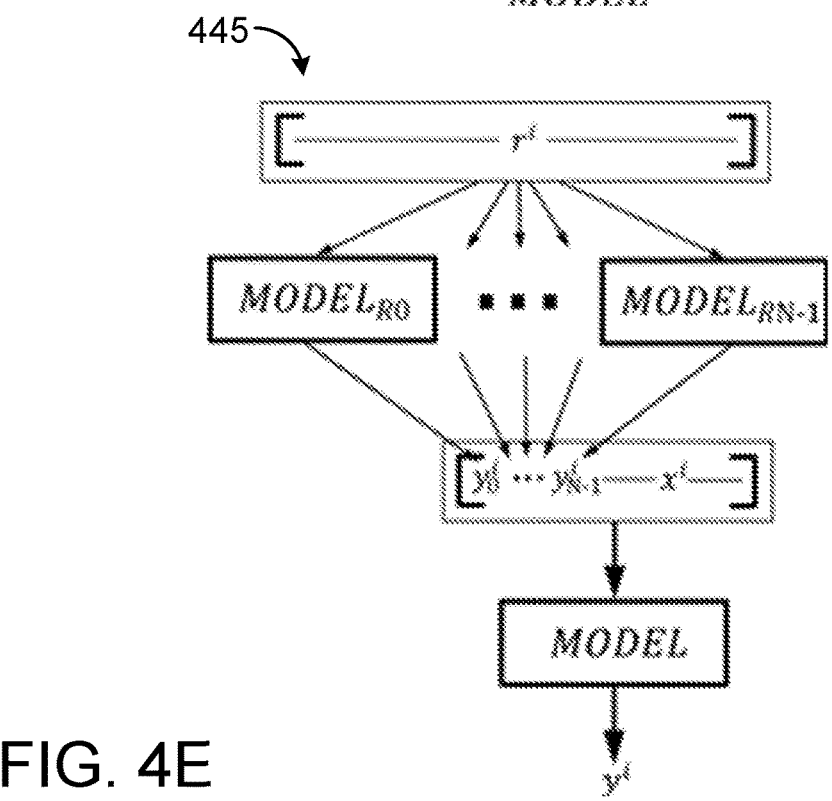

A training model for this approach is shown at 440 of FIG. 4E, in which N machine-learning models are trained for each of the EMR-based models. Once these machine-learning models are trained, they are run on the cohort data R to produce outputs for each of the subjects i. These initial risk scores are then concatenated with the device-derived dynamic features X to form the training data for the final model. A production model for this approach is shown at 445 of FIG. 4E. The N EMR-based models are run on the EMR data for the patient; their outputs, along with the features from the device, are then used as the features for the final model that produces the risk score.

In some examples, intermediate prediction variables may be used as input features to a machine-learning model. Rather than depending on clinicians or feature weights to pick the best features from the EMR data, such a machine-learning model involves creating an explicit set of intermediate variables that are targeted for prediction for risk. As an example, a decompensation risk model may be built from EMR data ($R^H$) with an intermediate stage directly before the output layer of risk that contains N nodes $y_0 \ldots y_{N-1}$. The output layer may then linearly combine these outputs and optionally apply a non-linearity. As a result, each of the N variables may be selected based on their ability to predict the target variable of decompensation risk. These variables may then be input as N additional features to the data in X as described. The choice of N may depend on the size of X, i.e., if there are 300 records and 10 features from X, there may be 20-30 variables in the penultimate layer.

Such an approach may be representative of the deep learning paradigm, where intermediate layers can produce useful representations. Additionally, the model may be cast in terms of Tibshirani's "Information Bottleneck," where a set of intermediate variables facilitate the prediction of a target variable based on an intermediate vector space. In this example, such approaches represent a means of doing effective data fusion of disparate data sources. In this way, a rich set of outputs from the EMR data are used that have been determined to be maximally predictive of risk. An additional benefit is that N can be easily adjusted by adjusting the first model's architecture. Given sufficient data capacity, the machine-learning model training may decide how to effectively utilize those variables, rather than having to manually determine a best set of features.

Figure 4F:
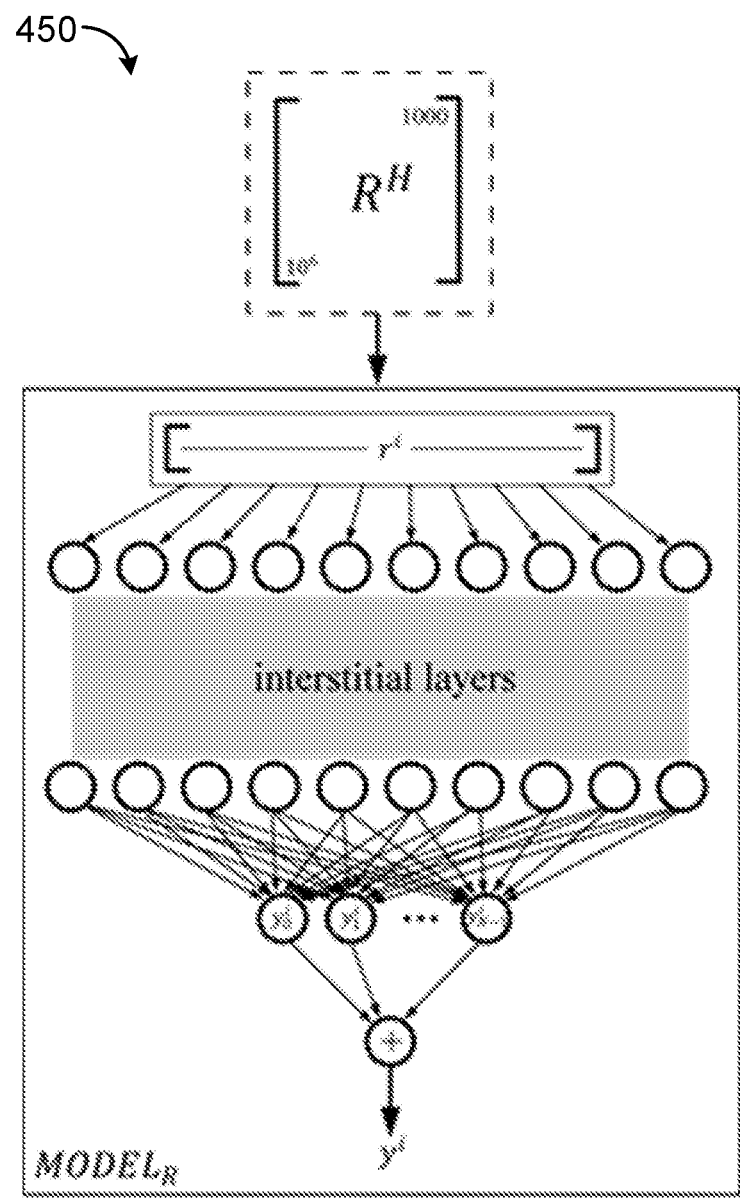
FIGS. 4F-4G show an example machine-learning model for predicting a risk of decompensated heart failure in a user using intermediate prediction variables as features.
Figure 4F:
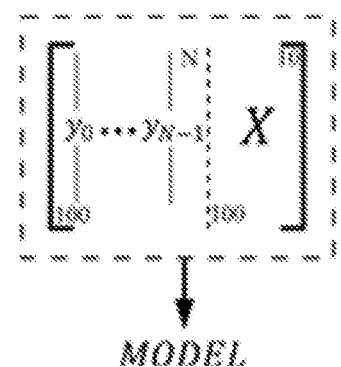

A training model for this approach is shown at 450 of FIG. 4F. There are two distinct models in this approach; the first is trained from all available EMR data, and is structured to have a set of N nodes in the penultimate layer. The variables in these nodes, $y_j$, are thus trained to be predictive of the target value (e.g., decompensation risk). Once this model is trained, it may be run on the current cohort data. The values of the $y_j$ are then concatenated with the device values in X to create the training data for the final model. Note that while the model at 450 is illustrated as a (deep) neural net, other models could be used. For instance, an ensemble model like a mixture of trees could be used, where the nodes $y_j$ are outputs from the individual members of the ensemble.

Figure 4G:
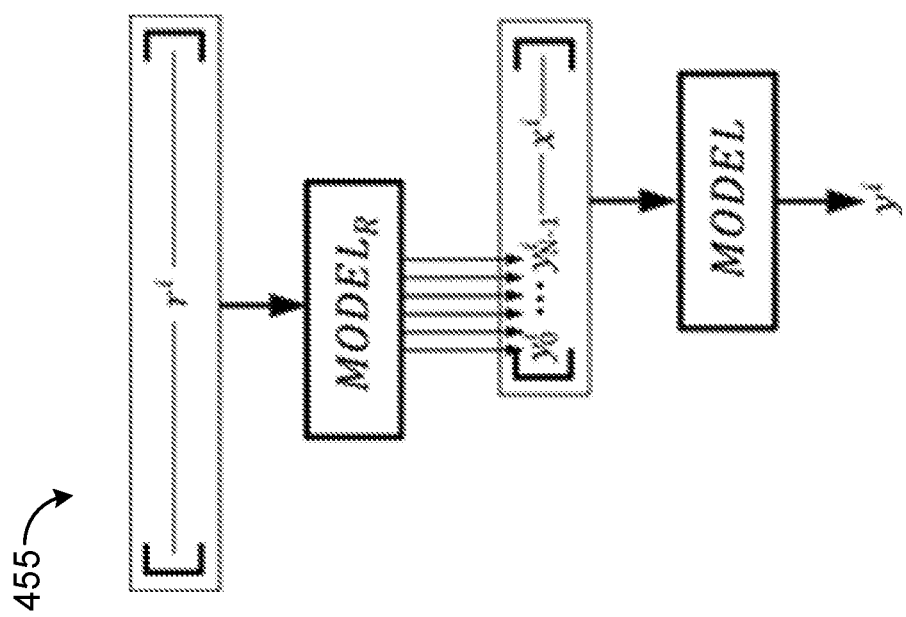

A production model for this approach is shown at 455 of FIG. 4G. The EMR records for the patient are first fed through the EMR model. The N intermediate values $y_j$ from the model are then concatenated with the features available from the device to form the feature vector for the final model.

For an individual patient, a system may thus be configured where a machine-learning model is generated based on the patient's static data at time of discharge as well as EMR records for numerous other patients. The static data and potentially dynamic data from other patients and any dynamic data acquired while the patient was under clinical care may also inform the machine-learning model. A set of classifiers for the dynamic data may then be used to evaluate incoming dynamic data for the patient over time and to determine a risk score for decompensation.

Figure 5:
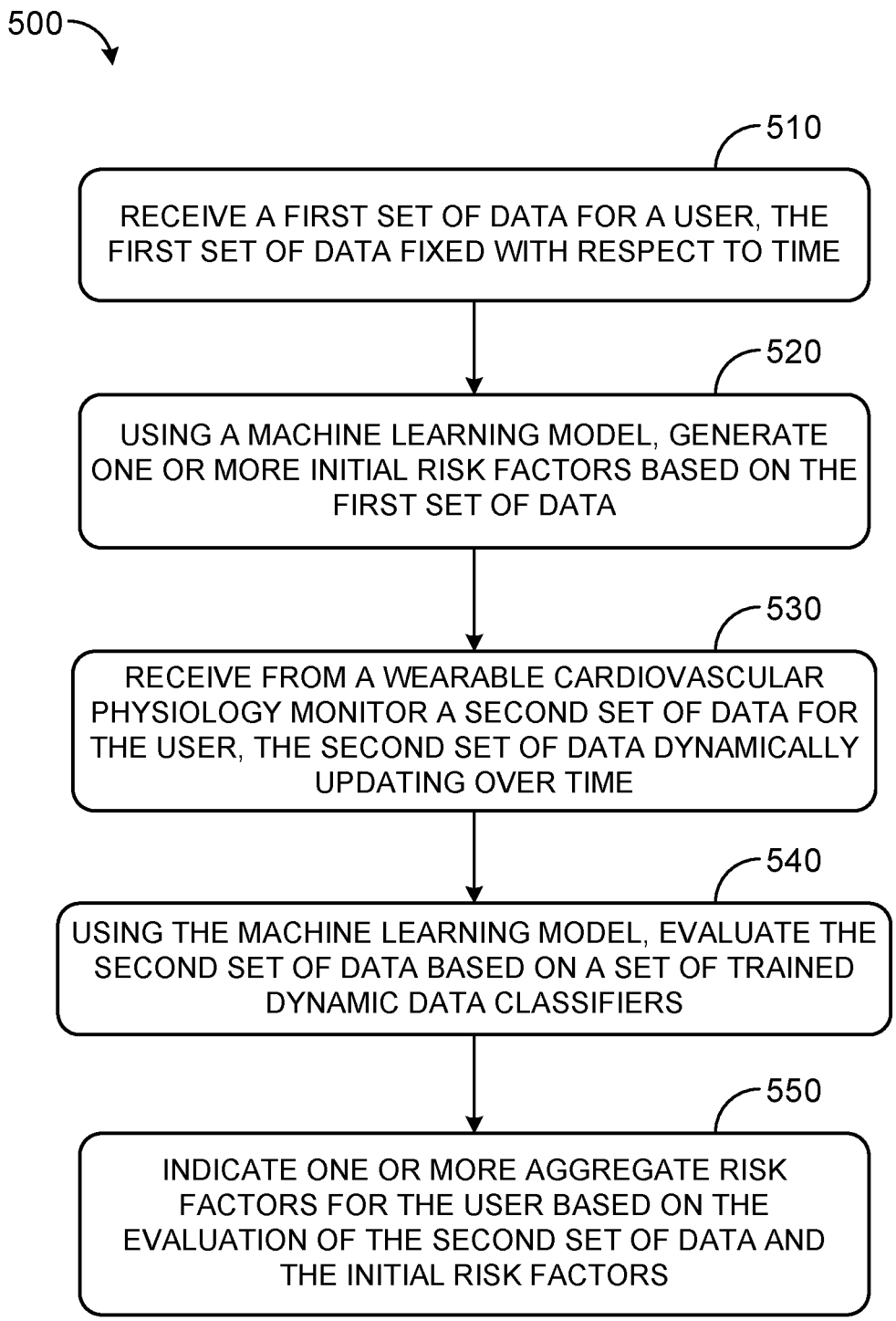
FIG. 5 shows an example method for determining a risk of decompensated heart failure in a user.

FIG. 5 shows an example method 500 for determining a risk of decompensated heart failure in a user. At 510, method 500 includes receiving a first set of data for the user, the first set of data fixed with respect to time. For example, the first set of data may comprise static, electronic medical record data for the user. As described with regard to FIG. 3, the first set of data may include patient demographic information, comorbidities, medications taken before, during, and after hospitalization, patient vital signs, patient lab results, patient weight change during hospitalization, echocardiogram results, etc. In some examples, the first set of data may include EMR data from one or individuals other than the user. For example, the first set of data may include EMR data from other patients within a current study cohort, and/or may include EMR data derived from historic medical records.

At 520, method 500 includes using machine-learning model to generate one or more initial risk factors based on the first set of data. For example, an initial risk factor may be generated for each feature within the first set of data, and/or a single initial risk factor may be generated for the entire first set of data. In some examples, a select set of features from the first set of data may be used to generate one or more initial risk factors.

At 530, method 500 includes receiving, from a wearable cardiovascular physiology monitor, a second set of data for the user, the second set of data dynamically updating over time. The wearable cardiovascular physiology monitor may be a wrist-worn cardiovascular physiology monitor. The second set of data may include, for example, information regarding the user's pulse arrival time, pulse transit time, heart rate, heart rate variability, and pulse pressure wave morphology. The pulse pressure wave morphology data may include information regarding the user's augmentation index, maximum systolic slope, systolic rise time, election time, dicrotic notch height, dicrotic notch timing, total pulse pressure, reflected wave arrival time, etc. Additional information within the second set of data may be included regarding the user's activity level, step count sleep time, sleep quality, posture, etc.

At 540, method 500 includes using the machine-learning model to evaluate the second set of data based on a set of trained dynamic data classifiers. For each feature of the dynamic data received from the wearable cardiovascular physiology monitor, the machine-learning model may apply classifiers indicating expected ranges of values for the feature. Such expected ranges of values may vary time, or may be variable based on one or more additional data points such as user's activity level, time since discharge, time since last medication, etc. The classifiers may be based on static data from the first data set indicating the user's expected dynamic features during compensation (e.g., at or immediately prior to discharge). As described with regard to FIG. 3, periodic data classifiers may also be generated so that periodically generated data may be evaluated by the machine-learning model and thus contribute to an aggregate risk score.

In some examples, evaluation of the second set of data against the dynamic data classifiers comprises an evaluation of a fixed history of dynamic features against the dynamic data classifiers. A machine-learning model may be configured as a discrete classifier that uses all of a user's first set of data as an input along with a fixed history (e.g., three days) of the user's second set of data, but does not make use of historical data from the second data set prior to that window. Users are typically stably compensated when they are discharged from the hospital and for up to several weeks subsequently. Probability of decompensation may thus be best predicted by monitoring a relatively short window of the second data set, so that a large amount of dynamic data collected when the user is in the compensated state does not overwhelm data representing early-stage decompensation.

As another example, the machine-learning model may make a Markov assumption. In other words, the machine-learning model may assume that all of the dependence in previous time steps is captured in the previous model's output. With this assumption, to predict a decompensation risk at time t, the machine-learning model may only look at dynamic data associated with time t, along with the model output from time t−1. The first set of data may be reincorporated at each time step, and/or may factor explicitly only into the initial output $t_0$ and would then be implicitly carried forward in the model output.

At 550, method 500 includes indicating one or more aggregate risk scores for the user based on an evaluation of the second set of data against the dynamic data classifiers and the initial risk factors described with regard to 520. The one or more aggregate risk scores may indicate a risk of decompensation within a set window of time. For example, a risk score may be indicated for the upcoming 24 hours, the upcoming week, the upcoming 30 days, etc. As described with regard to FIG. 3, the risk score may be presented to the user via the wearable cardiovascular physiology monitor and/or a secondary computing device. The risk score may also be presented to a clinician. Additional alerts based at least on the risk score may be presented to the user and/or clinician to influence the user's treatment.

Risk scores, both initial and aggregate, dynamic and static input data, and intermediate analysis data (such as confidence levels, regressions, etc.) may be saved in one or more databases, either locally, at a cloud computing device, or a remote computing device. Saved data may be analyzed to improve machine-learning models, both for the user as well as other users, such as users within a study cohort, and/or users with a same monitoring.

Over time, the comparison of dynamic data to dynamic data classifiers may provide an accurate depiction of a user's risk of decompensation. However, there may be scenarios wherein the user's activity affects the dynamic data without physiologically affecting their risk of decompensation. As an example, medications typically given to heart failure patients (e.g., rate limiters, diuretics, vasodilators) have a significant acute effect that can be observed within dynamic data generated by a wearable cardiovascular physiology monitor. As such, it is important to recognize events such as medication ingestion, both to prevent from erroneous risk score reporting, and to accurately evaluate the user during medicated and unmedicated states. In this way, short-term fluctuations in dynamic data signals may be properly interpreted or ignored.

Figure 6:
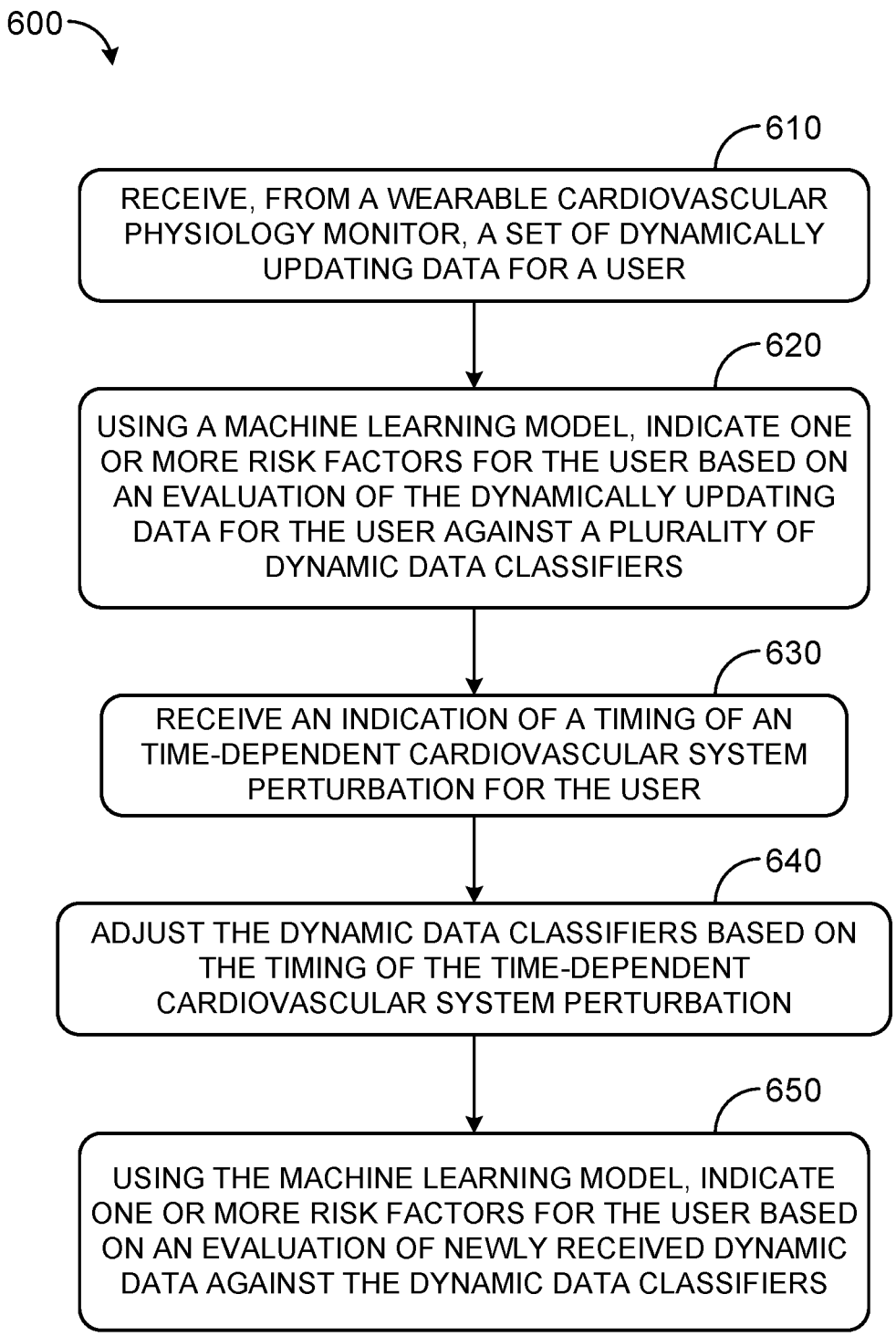
FIG. 6 shows an example method for determining a risk of decompensated heart failure in a user.

FIG. 6 shows an example method 600 for determining a risk of decompensated heart failure in a user. At 610, method 600 includes receiving, from a wearable cardiovascular physiology monitor, a set of dynamically-updating data for the user. As described with regard to FIG. 3, the dynamically-updating data may include pulse arrival time, pulse transit time, heart rate, heart rate variability, pressure wave morphology, activity level, step count, sleep time, sleep quality, posture, etc.

At 620, method 600 includes, using a machine-learning model to indicate one or more risk scores for the user based on an evaluation of the dynamically-updating data for the user against a plurality of dynamic data classifiers. A default set of dynamic data classifiers may be selected to evaluate the dynamically-updating data, the default set of classifiers representing an aggregate set of static and dynamic data for the user that is applicable during most user states.

At 630, method 600 includes receiving an indication of a timing of a time-dependent cardiovascular system perturbation for the user. For example a time-dependent cardiovascular system perturbation for the user include a heart arrhythmia, a physical activity performed by the user, a therapeutic treatment received by the user, a pacemaker pulsation or an ingestion of medication by the user. Additional time-dependent cardiovascular system perturbations may include events that produce a predictable change in one or ore cardiovascular parameters that may in turn produce a predictable change in one or more dynamically-updating features. A predictable change may be observable over a finite duration, whereby the perturbed cardiovascular parameter and/or dynamically-updating feature may return to a baseline value over time.

A time-dependent cardiovascular system perturbation may be directly indicated by the user, and/or automatically inferred. In some examples, the user may provide direct indication of medication ingestion, via a wearable cardiovascular physiology monitor or secondary computing device, for example. In other examples, medication ingestion may be automatically inferred based on received dynamic data. For example, the reflected wave arrival time (RWAT) may change following medication ingestion. Such a feature change may be identified in the dynamic data and used to infer medication ingestion. If the user is consistently providing a direct indication of medication, multiple such features may be specifically identified, increasing the accuracy of the inference. The user may train the model while under clinical care, and such data may be incorporated into the static data set for the user.

At 640, method 600 includes adjusting the dynamic data classifiers based on a tinning of the time-dependent cardiovascular system perturbation. For example, a secondary set of dynamic data classifiers may be utilized following the time-dependent cardiovascular system perturbation. As one example, dicrotic notch height may be affected following medication ingestion, and then gradually return to a normal height over time. As such, "time since last dose" may be a feature incorporated into the machine-learning model that is used to adjust dynamic data classifiers following medication ingestion. Dynamic data collected during the post-medication ingestion period may be utilized to evaluate the effectiveness and/or any unexpected effects of the medication. These results may be reported to the clinic.

As such, at 650, method 600 includes using the machine-learning model to indicate one or more risk scores for the user based on an evaluation of newly received dynamic data against the adjusted dynamic data classifiers. For example, a user may present as healthy (or healthier) following medication ingestion. Evaluating subsequent dynamic data against a default set of dynamic data classifiers may result in inaccurate risk scores and incorrect treatment decisions, whether made automatically or by a clinician. Risk scores may also be affected by a lack of medication ingestion, as non-compliance with prescriptions is a strong indicator of negative outcomes. For medications that produce a spike-and-degrade profile in one or more dynamic features, the absence of a spike may be an indicator of a missed dose. For medications that have a time-release or steady-state effect, a degradation from the expected dynamic features may indicate a missed dose. Inference of a missed dose may be used to trigger an alert or reminder to the user.

Figure 7:
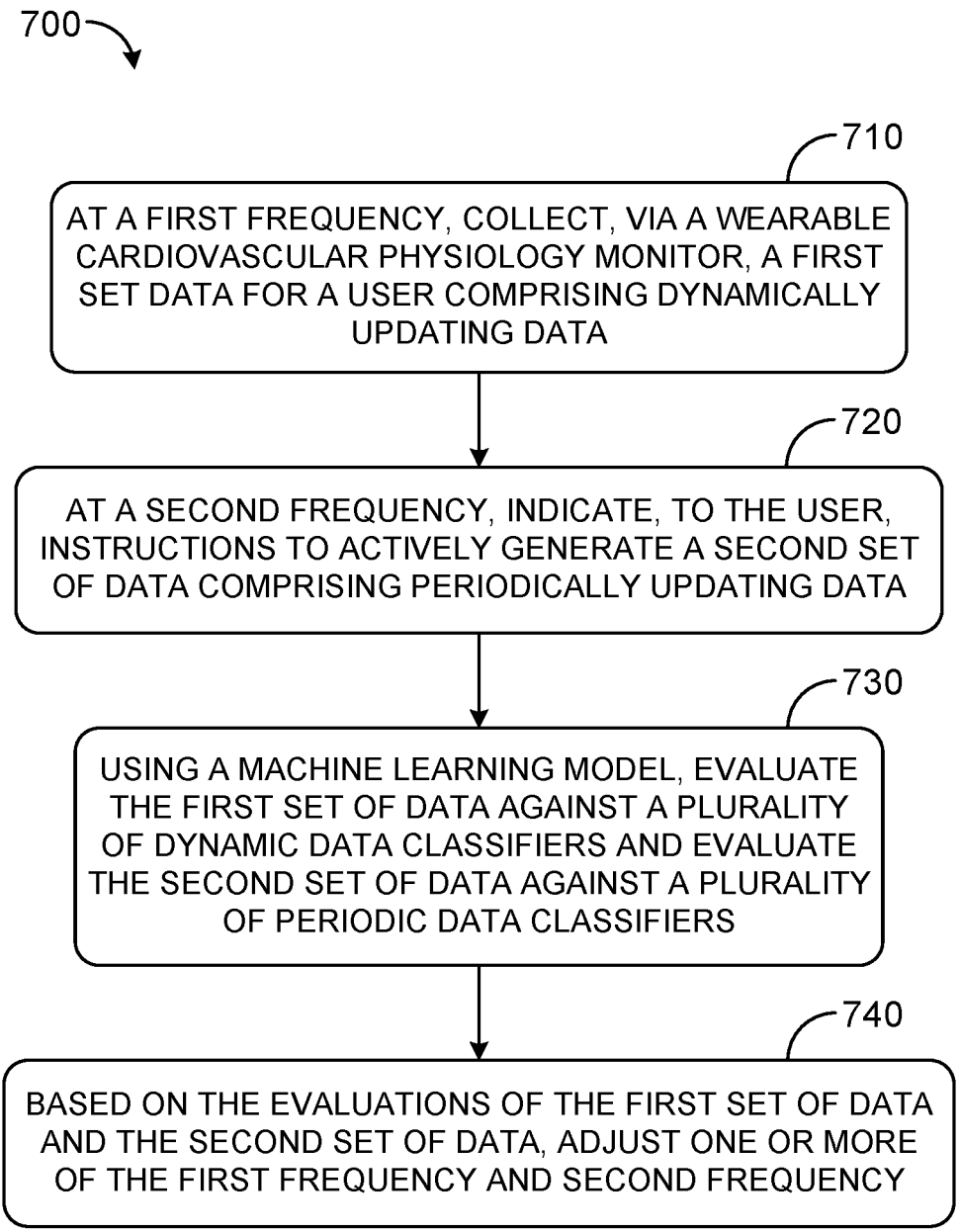
FIG. 7 shows an example method for monitoring heart health of a user.

Physiological data, along with clinical data and patient-reported symptom data, may be used not only to predict outcomes, but also to intelligently change the rate and timing at which physiological measurements and symptom reports are taken. For example, FIG. 7 shows an example method 700 for monitoring heart health of a user. At 710, method 700 includes, collecting, at a first frequency, from a wearable cardiovascular physiology monitor, a first set of data for the user comprising dynamically-updating data. At 720, method 700 includes indicating instructions to the user at a second frequency, less than the first frequency, to actively generate a second set of data comprising periodically-updating data. As described with regard to FIG. 3, generating periodically-updating data may require the patient to perform a task, such as standing still for 30 seconds, standing up from a sitting position, touching or adjusting a wearable or secondary health monitoring device, sitting near a bedside sensor, etc.

At 730, method 700 includes using machine-learning model to evaluate the first set of data against a plurality of dynamic data classifiers, and evaluating the second set of data against a plurality of periodic data classifiers. At 740, method 700 includes, based on the evaluations of the first set of data and the second set of data, adjusting one or more of the first frequency and the second frequency.

For example, if the evaluation of the first and second sets of data indicates a risk of early-stage decompensation but with low confidence, the user may be instructed to increase the frequency at which periodic data is actively generated. Additionally or alternatively, the device may be re-configured to more frequently collect passive data (i.e., data whose collection does not require user participation). Further, the frequency of alerts and/or data reports to the user's clinician may be increased.

As another example, if the evaluation of the first and second sets of data indicates that the user is exiting a high-risk stage and is stabilizing, the user may be instructed to decrease the frequency at which periodic data is actively generated. In some examples, the device may be re-configured to less frequently collect passive data. Reducing the burden on the user to actively generate periodic data may improve compliance and reduce patient taxation. Reducing the frequency at which passive data is collected may extend the device's battery life.

In some examples, the user may be instructed to adjust the frequency at which one or more periodic data features are actively generated, while instructed to maintain the frequency at which other periodic data features are actively generated. For example, the most burdensome and/or least informative periodic measurements may be decreased in an effort to increase user compliance with the remaining periodic measurements.

In another example, the frequency at which dynamic data is collected may be modified. For example, many HF patients report symptoms only during periods of increased exercise. Based on data collected from accelerometers/gyroscopes, periods of exercise may be identified, and dynamic data collection may be increased during these periods. Similarly, if the user shows limited symptoms during sleep or rest, the dynamic data collection may be decreased during these periods. In this way, power consumption by the wearable cardiovascular physiology monitor may be reduced.

As evident from the foregoing description, the methods and processes described herein may be tied to a sensor-and-logic system of one or more machines. Such methods and processes may be implemented as a computer-application program or service, an application-programming interface (API), a library, firmware, and/or other computer-program product. FIG. 2 shows one, non-limiting example of a sensor-and-logic system to enact the methods and processes described herein. However, these methods and process may also be enacted on sensor-and-logic systems of other configurations and form factors, as shown schematically in FIG. 8.

Figure 8:
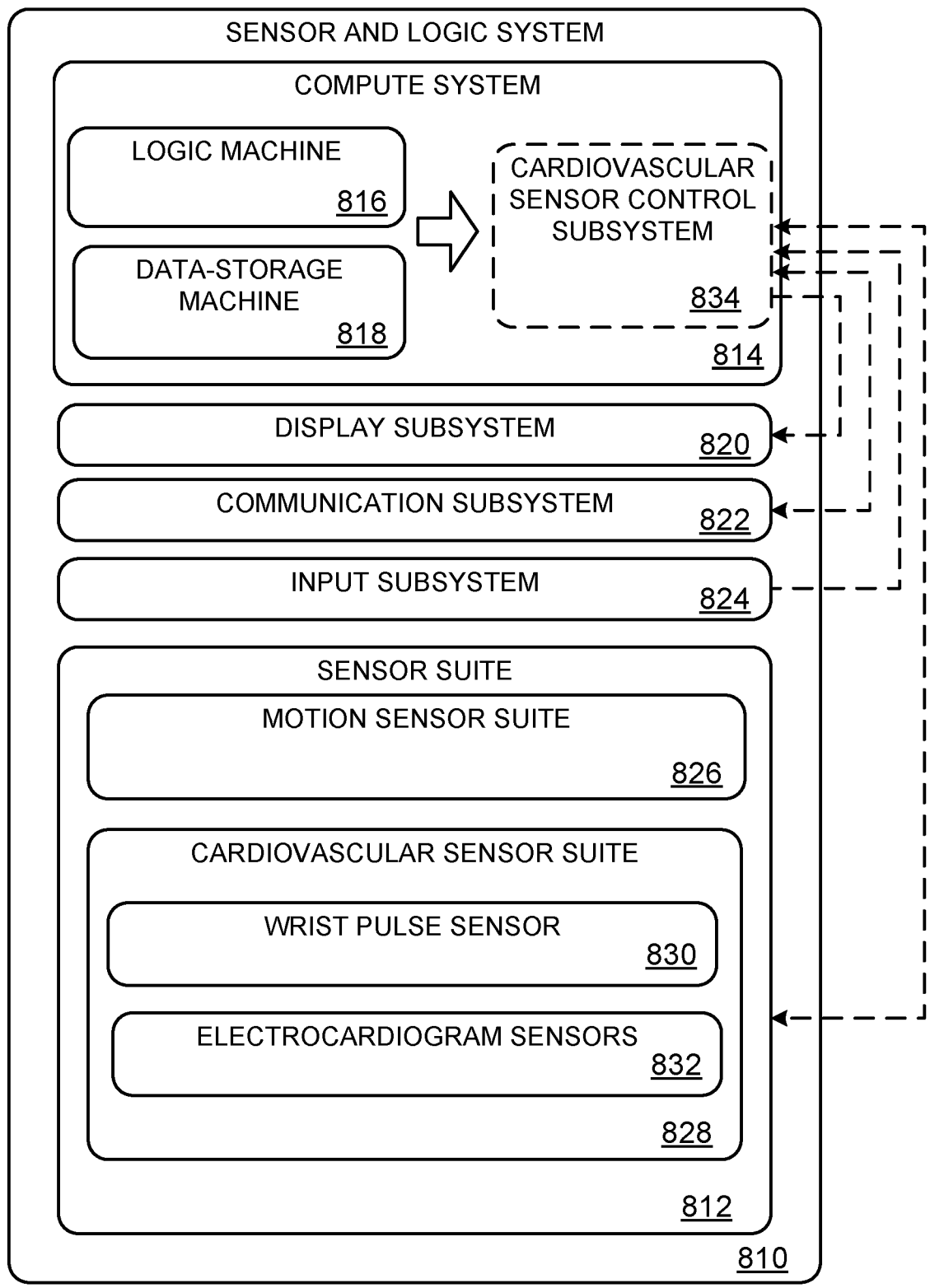
FIG. 8 schematically shows a sensor-and-logic system usable to determine a risk of decompensated heart failure in a user.

FIG. 8 schematically shows a form-agnostic sensor-and-logic system 810 that includes a sensor suite 812 operatively coupled to a compute system 814. The compute system includes a logic machine 816 and a data-storage machine 818. The compute system is operatively coupled to a display subsystem 820, a communication subsystem 822, an input subsystem 824, and/or other components not shown in FIG. 8.

Logic machine 816 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 816 may include one or more processors configured to execute software instructions. Additionally or alternatively, the logic machine may include one or more hardware or firmware logic machines configured to execute hardware or firmware instructions. Processors of the logic machine may be single-core or multicore, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 818 includes one or more physical devices configured to hold instructions executable by logic machine 816 to implement the methods and processes described herein. When such methods and processes are implemented, the state of the data-storage machine may be transformed—e.g., to hold different data. The data-storage machine may include removable and/or devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 818 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 816 and data-storage machine 818 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 820 may be used to present a visual representation of data held by data-storage machine 818. This visual representation may take the form of a graphical user interface (GUI). As the herein described methods and processes change the data held by the storage machine, and thus transform the state of the storage machine, the state of display subsystem 820 may likewise be transformed to visually represent changes in the underlying data. Display subsystem 820 may include one or more display subsystem devices utilizing virtually any type of technology. Such display subsystem devices may be combined with logic machine 816 and/or data-storage machine 818 in a shared enclosure, or such display subsystem devices may be peripheral display subsystem devices. Display 234 of FIG. 2 is an example of display subsystem 820.

Communication subsystem 822 may be configured to communicatively couple compute system 814 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 236 of FIG. 2 is an example of communication subsystem 822.

Input subsystem 824 may comprise or interface with one or more user-input devices such as a keyboard, touch screen, button, dial, joystick, or switch. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition. Push button 248 of FIG. 2 is an example of input subsystem 824.

Sensor suite 812 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIG. 2. Sensor suite 812 may include motion sensor suite 826 and cardiovascular sensor suite 828. Motion sensor suite 826 may include one or more of an accelerometer, gyroscope, magnetometer, or other suitable motion detectors.

As described herein, cardiovascular sensor suite may include wrist pulse sensor 830 and electrocardiogram sensors 832, as well as one or more microphones. Compute system 814 may include cardiovascular sensor control subsystem 834, which may be communicatively coupled to logic machine 816 and data-storage machine 818, as well as sensor suite 812. Wrist pulse sensor 830 may include a pressure transducer comprising one or more piezo-resistive sensors configured to provide absolute pressure signals to compute system 814 via an analog-to-digital converter. Such a pressure transducer may be configured to transduce pressure waves from the radial artery through the skin of the wearer. Wrist pulse sensor 830 may additionally or alternatively include an optical pulse sensor. An optical pulse sensor may comprise an optical source, such as one or more LED emitters, for example, and may further comprise an optical sensor including one or more photodiodes matched to detect light at frequencies that are based on the frequencies of light output by the optical source. The optical source may be configured to illuminate one or more blood vessels through the skin of the wearer, and the optical sensor may be configured to measure illumination reflected from or transmitted through blood vessels.

Electrocardiogram sensors 832 may include one or more contact sensor modules that may include independent or cooperating sensor elements. The contact sensor modules may provide an electrical resistance and/or capacitance sensory function, which measures the electrical resistance and/or capacitance of the wearer's skin. Electrocardiogram sensors 832 may provide absolute resistance and/or capacitance signals to compute system 814 via an analog-to-digital converter.

Cardiovascular sensor control subsystem 834 may further receive raw signals from one or more microphones, cameras, accelerometers, gyroscopes, other components of sensor suite 812, as well as raw and/or pre-processed signals received from components of input subsystem 824, and raw and/or pre-processed signals received from components of communication subsystem 822. Cardiovascular sensor control subsystem 834 may process the raw and/or pre-processed signals to determine heart rate, blood pressure, caloric expenditures, pulse transit time, pulse wave velocity, heart pre-ejection period, radial pulse arrival time, etc. Processed signals may be stored and output via compute system 814. Control signals sent to sensor suite 812 may be based on signals received from sensor suite 812, information stored in data-storage machine 818, input received from communication subsystem 822, input received from input subsystem 824, etc. Processed signals may be transmitted via display subsystem 820 and/or communication subsystem 822. As described herein, cardiovascular sensor control subsystem 834 may include a plurality of subsystems, such as a pulse-transit time monitor, an electrode-positioning sensor subsystem, one or more controllers, and one or more user interfaces.

In one example, a method for determining a risk of decompensated heart failure in a user comprises receiving a first set of data for the user, the first set of data fixed with respect to time; using a machine-learning model, generating one or more initial risk factors based on the first set of data; receiving, from a wearable cardiovascular physiology monitor, a second set of data for the user, the second set of data dynamically updating over time; using the machine-learning model, evaluating the second set of data based on a set of trained dynamic data classifiers; and indicating one or more aggregate risk scores for the user based on the evaluation of the second set of data against the dynamic data classifiers and the initial risk factors. In this example, or any other example, the first set of data comprises electronic medical records for the user. In this example, or any other example, the first set of data comprises electronic medical records for one or more other users. In this example, or any other example, the set of data comprises one or more pulse pressure wave morphology features. In this example, or any other example, evaluation of the second set of data against the dynamic data classifiers comprises an evaluation of a fixed history of dynamic features against the dynamic data classifiers. In this example, or any other example, evaluation of the second set of data against the dynamic data classifiers comprises evaluation of dynamic features against the dynamic data classifiers using a Markov assumption for the dynamic features. In this example, or any other example, the one or more aggregate risk scores indicate a risk of decompensation within a set window of time. In this example, or any other example an alert is indicated to the user based on the one or more aggregate risk scores.

In another example, a method for determining a risk of decompensated heart failure in a user comprises: receiving, from a wearable cardiovascular physiology monitor, a set of dynamically-updating data for the user; using a machine-learning model, indicating one or more risk scores for the user based on an evaluation of the dynamically-updating data for the user against a plurality of dynamic data classifiers; receiving an indication of a timing of a time-dependent cardiovascular system perturbation for the user; adjusting the dynamic data classifiers based on the timing of the time-dependent cardiovascular system perturbation; and using the machine-learning model, indicating one or more risk scores for the user based on an evaluation of newly received dynamic data against the adjusted dynamic data classifiers. In this example, or any other example, the dynamic data classifiers are adjusted based on a time since the time-dependent cardiovascular system perturbation. In this example, or any other example, receiving an indication of a timing of a time-dependent cardiovascular system perturbation for the user includes inferring the time-dependent cardiovascular system perturbation based on an evaluation of dynamic data against dynamic data classifiers. In this example, or any other example, inferring a time-dependent cardiovascular system perturbation based on an evaluation of dynamic data against dynamic data classifiers includes evaluating one or more pulse pressure wave morphology features against an expected pulse pressure wave morphology feature. In this example, or any other example, the dynamic data classifiers are adjusted based on an evaluation of dynamic data received following a known time-dependent cardiovascular system perturbation. In this example, or any other example receiving an indication of a timing of a time-dependent cardiovascular system perturbation for the user includes receiving an indication of a timing of an ingestion of medication by the user. In this example, or any other example, receiving an indication of a timing of an ingestion of medication by the user includes actively receiving an indication of medication ingestion as an input to the wearable cardiovascular physiology monitor. In this example, or any other example, the method further comprises receiving an indication that medication was not ingested by the user during a predetermined window; adjusting the dynamic data classifiers based on a lack of ingestion of medication; and using the machine-learning model, indicating one or more risk scores for the user based on an evaluation of newly received dynamic data against the adjusted dynamic data classifiers.

In yet another example, a method for monitoring heart health of a user comprises: at a first frequency, collecting, via a wearable cardiovascular physiology monitor, a first set of data for the user comprising dynamically-updating data; at a second frequency, indicating, to the user, instructions to actively generate a second set of data comprising periodically-updating data; using a machine-learning model, evaluating the first set of data against a plurality of dynamic data classifiers and evaluating the second set of data against a plurality of periodic data classifiers; and based on the evaluations of the first set of data and the second set of data, adjusting one or both of the first frequency and the second frequency. In this example, or any other example, actively generating a second set of data comprising periodically-updating data includes the user actively interacting with one or more health monitoring devices for a duration. In this example, or any other example, the evaluations of the first set of data and the second set of data indicate an increased risk of decompensated heart failure, and wherein adjusting one or both of the first frequency and the second frequency includes increasing one or both of the first frequency and the second frequency. In this example, or any other example, the evaluations of the first set of data and the second set of data indicate a decreased risk of decompensated heart failure, and wherein adjusting one or both of the first frequency and the second frequency includes decreasing one or both of the first frequency and the second frequency.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for determining a risk of decompensated heart failure in a user, comprising:
   using a machine-learning model, generating one or more initial risk factors based on a static set of data, and generating an explicit set of intermediate variables targeted for prediction for risk, the explicit set of intermediate variables including variables from a penultimate layer of nodes of the machine-learning model;
   receiving, from a wearable cardiovascular physiology monitor, a set of dynamically-updating data for the user;
   using the machine-learning model, indicating one or more risk scores for the user based on an evaluation of a set of dynamic features of the dynamically-updating data for the user concatenated with the explicit set of intermediate variables, the set of dynamic features evaluated against a plurality of default dynamic data classifiers independently of the initial risk factors;
   receiving an indication of a timing of a time-dependent cardiovascular system perturbation for the user;
   adjusting the default dynamic data classifiers based on the timing of the time-dependent cardiovascular system perturbation;
   using the machine-learning model, indicating one or more updated risk scores for the user based on an evaluation of dynamic features included in newly received dynamically-updating data against the adjusted dynamic data classifiers; and
   based on the timing of the time-dependent cardiovascular system perturbation, evaluating dynamic features included in subsequently received dynamically-updating data against the default dynamic data classifiers.

2. The method of claim 1, wherein the default dynamic data classifiers are adjusted based on a time since the time-dependent cardiovascular system perturbation.

3. The method of claim 1, wherein receiving the indication of the timing of the time-dependent cardiovascular system perturbation for the user includes inferring the time-dependent cardiovascular system perturbation based on the evaluation of dynamic features included in the dynamically-updating data against default dynamic data classifiers.

4. The method of claim 3, wherein inferring the time-dependent cardiovascular system perturbation based on the evaluation of dynamic features included in the dynamically-updating data against default dynamic data classifiers includes evaluating one or more pulse pressure wave morphology features against an expected pulse pressure wave morphology feature.

5. The method of claim 1, wherein the default dynamic data classifiers are adjusted based on an evaluation of dynamic features included in the dynamically-updating data received following a known time-dependent cardiovascular system perturbation.

6. The method of claim 1, wherein receiving the indication of the timing of the time-dependent cardiovascular system perturbation for the user includes receiving an indication of a timing of an ingestion of medication by the user.

7. The method of claim 6, wherein receiving the indication of the timing of the ingestion of medication by the user includes actively receiving an indication of medication ingestion as an input to the wearable cardiovascular physiology monitor.

8. The method of claim 6, further comprising:
   receiving an indication that medication was not ingested by the user during a predetermined window;
   adjusting the default dynamic data classifiers based on a lack of ingestion of medication; and
   using the machine-learning model, indicating one or more risk scores for the user based on an evaluation of dynamic features included in newly received dynamically-updating data against the adjusted dynamic data classifiers.

9. A system for determining a risk of decompensated heart failure for a user, comprising:
   a wearable cardiovascular physiology monitor; and
   a compute system configured to host a machine-learning model, the compute system configured to:
      using the machine-learning model, generate one or more initial risk factors based on a static set of data, and generate an explicit set of intermediate variables targeted for prediction for risk, the explicit set of intermediate variables including variables from a penultimate layer of nodes of the machine-learning model;
      receive, from the wearable cardiovascular physiology monitor, a set of dynamically-updating data for the user;
      using the machine-learning model, indicate one or more risk scores for the user based on an evaluation of a set of dynamic features of the dynamically-updating data for the user concatenated with the explicit set of intermediate variables, the set of dynamic features evaluated against a plurality of default dynamic data classifiers independently of the initial risk factors;
      receive an indication of a timing of a time-dependent cardiovascular system perturbation for the user;
      adjust the default dynamic data classifiers based on the timing of the time-dependent cardiovascular system perturbation;
      using the machine-learning model, indicate one or more updated risk scores for the user based on an evaluation of dynamic features included in newly received dynamically-updating data against the adjusted dynamic data classifiers; and
      based on the timing of the time-dependent cardiovascular system perturbation, evaluate dynamic features included in subsequently received dynamically-updating data against the default dynamic data classifiers.

10. A data-storage machine holding instructions executable by a compute system to determine a risk of decompensated heart failure for a user, comprising:
    instructions to use a machine-learning model to generate one or more initial risk factors based on a static set of data, and to generate an explicit set of intermediate variables targeted for prediction for risk, the explicit set of intermediate variables including variables from a penultimate layer of nodes of the machine-learning model;
    instructions to receive, from a wearable cardiovascular physiology monitor, a set of dynamically-updating data for the user;
    instructions to use the machine-learning model to indicate one or more risk scores for the user based on an evaluation of a set of dynamic features of the dynamically-updating data for the user concatenated with the explicit set of intermediate variables, the set of dynamic features evaluated against a plurality of default dynamic data classifiers independently of the initial risk factors;
instructions to receive an indication of a timing of a time-dependent cardiovascular system perturbation for the user;
instructions to adjust the default dynamic data classifiers based on the timing of the time-dependent cardiovascular system perturbation;
instructions to use the machine-learning model to indicate one or more updated risk scores for the user based on an evaluation of dynamic features included in newly received dynamically-updating data against the adjusted dynamic data classifiers; and
instructions to, based on the timing of the time-dependent cardiovascular system perturbation, evaluate dynamic features included in subsequently received dynamically-updating data against the default dynamic data classifiers.

* * * * *